(12) United States Patent
Coates et al.

(10) Patent No.: US 6,366,087 B1
(45) Date of Patent: Apr. 2, 2002

(54) NMR LOGGING APPARATUS AND METHODS FOR FLUID TYPING

(76) Inventors: George Richard Coates, 440 FM 2754, Bellville, TX (US) 78746; Lei Bob Hou, 1602 Enclave Pkwy. #1510, Houston, TX (US) 77077

( * ) Notice: Subject to any disclaimer, the term of this patent is extended or adjusted under 35 U.S.C. 154(b) by 0 days.

(21) Appl. No.: 09/429,293

(22) Filed: Oct. 28, 1999

Related U.S. Application Data

(60) Provisional application No. 60/106,259, filed on Oct. 30, 1998.

(51) Int. Cl.[7] ................................................. G01V 3/00
(52) U.S. Cl. ........................................ 324/303; 324/300
(58) Field of Search ............................... 324/303, 300, 324/307, 318

(56) References Cited

U.S. PATENT DOCUMENTS

| | | |
|---|---|---|
| 1,158,959 A | 11/1915 | Beach |
| 2,912,641 A | 11/1959 | Ruble |
| 2,973,471 A | 2/1961 | Armistead et al. |
| 3,205,477 A | 9/1965 | Kalbfell |
| 3,213,357 A | 10/1965 | Brown et al. |
| 3,360,716 A | 12/1967 | Bloom et al. |
| 3,395,337 A | 7/1968 | Varian |
| 3,402,344 A | 9/1968 | Brown et al. |
| 3,453,433 A | 7/1969 | Alger et al. ................ 250/83.3 |
| 3,508,438 A | 4/1970 | Alger et al. .................. 73/152 |
| 3,567,935 A | 3/1971 | Nagel ........................ 250/83.1 |
| 3,567,936 A | 3/1971 | Tittman ..................... 250/83.1 |
| 3,590,228 A | 6/1971 | Burke .................... 235/151.35 |
| 3,593,116 A | 7/1971 | Culpepper .................. 324/0.5 |
| 3,617,867 A | 11/1971 | Herzog ....................... 324/0.5 |
| 3,638,484 A | 2/1972 | Tixier .......................... 73/152 |
| 3,657,730 A | 4/1972 | Robinson et al. ............ 324/0.5 |
| 3,667,035 A | 5/1972 | Slichter .................... 324/0.5 R |
| 3,777,560 A | 12/1973 | Guignard ................... 73/151.5 |
| 3,784,898 A | 1/1974 | Darley et al. ............ 324/0.5 R |
| 3,896,668 A | 7/1975 | Anderson et al. ............. 73/152 |

(List continued on next page.)

FOREIGN PATENT DOCUMENTS

| | | | |
|---|---|---|---|
| EP | 0 295 134 A2 | 12/1988 | G01V/3/32 |
| EP | 0 581 666 A3 | 2/1994 | G01V/3/32 |
| EP | 0 649 035 B1 | 4/1995 | G01V/3/32 |
| GB | 2 056 082 A | 7/1980 | G01N/24/08 |
| WO | WO 92/10768 | 6/1992 | G01V/3/32 |
| WO | WO 98/25164 | 6/1998 | G01V/3/32 |

OTHER PUBLICATIONS

Akkurt et al., "Selection of Optimal Acquisition Parameters for MRIL Logs," SPWLA 37th Annual Logging Symposium, Jun. 16–19, 1996.

Akkurt et al., "NMR Logging of Natural Gas Reservoirs," SPWLA 36th Annual Logging Symposium (Jun. 26–29, 1995).

(List continued on next page.)

*Primary Examiner*—Jay Patidar
*Assistant Examiner*—Brij B. Shrivastav
(74) *Attorney, Agent, or Firm*—Pennie & Edmonds LLP

(57) ABSTRACT

A novel method and apparatus is disclosed for the separation of fluid phases in NMR borehole measurements. The method is based on selecting an optimum contrast mechanism and a corresponding set of measurement parameters for a particular borehole environment. The contrast mechanism can be based on diffusion, relaxation time or hydrogen index differences between different types of fluids. Once an initial measurement is made, the measurement parameters are compared to a predetermined set of values to broadly estimate the types of fluids present in the geologic environment. If necessary, the measurement is repeated to obtain optimal fluid typing for the estimated fluid types.

34 Claims, 10 Drawing Sheets

U.S. PATENT DOCUMENTS

| | | | |
|---|---|---|---|
| 4,291,271 A | 9/1981 | Lauffer | 324/307 |
| 4,310,887 A | 1/1982 | Suau | 364/422 |
| 4,350,955 A | 9/1982 | Jackson et al. | 324/303 |
| 4,479,564 A | 10/1984 | Tanguy | 181/105 |
| 4,528,508 A | 7/1985 | Vail, III | 324/303 |
| 4,536,714 A | 8/1985 | Clark | 324/338 |
| 4,629,986 A | 12/1986 | Clow et al. | 324/303 |
| 4,656,422 A | 4/1987 | Vail, III et al. | 324/303 |
| 4,686,364 A | 8/1987 | Herron | 250/256 |
| 4,707,658 A | 11/1987 | Frahm et al. | 324/309 |
| 4,710,713 A | 12/1987 | Taicher et al. | 324/303 |
| 4,714,881 A | 12/1987 | Givens | 324/303 |
| 4,717,876 A | 1/1988 | Masi et al. | 324/303 |
| 4,717,877 A | 1/1988 | Taicher et al. | 324/303 |
| 4,717,878 A | 1/1988 | Taicher et al. | 324/303 |
| 4,728,892 A | 3/1988 | Vinegar et al. | 324/309 |
| 4,785,245 A | 11/1988 | Lew et al. | 324/308 |
| 4,792,757 A | 12/1988 | Vail, III et al. | 324/303 |
| RE32,913 E | 4/1989 | Clark | 324/338 |
| 4,825,163 A | 4/1989 | Yabusaki et al. | 324/318 |
| 4,829,252 A | 5/1989 | Kaufman | 324/309 |
| 4,875,013 A | 10/1989 | Murakami et al. | 324/318 |
| 4,885,540 A | 12/1989 | Snoddy et al. | 324/318 |
| 4,899,112 A | 2/1990 | Clark et al. | 324/338 |
| 4,933,638 A | 6/1990 | Kenyon et al. | 324/303 |
| 4,933,640 A | 6/1990 | Kuckes | 324/339 |
| 4,949,045 A | 8/1990 | Clark et al. | 324/338 |
| 4,987,368 A | 1/1991 | Vinegar | 324/303 |
| 4,994,777 A | 2/1991 | Leupold et al. | 335/302 |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg et al. | 324/303 |
| 5,122,746 A | 6/1992 | King et al. | 324/307 |
| 5,138,263 A | 8/1992 | Towle | 324/338 |
| 5,200,699 A | 4/1993 | Baldwin et al. | 324/303 |
| 5,212,447 A | 5/1993 | Paltiel | 324/300 |
| 5,235,285 A | 8/1993 | Clark et al. | 324/342 |
| 5,280,243 A | 1/1994 | Miller | 324/303 |
| 5,291,137 A | 3/1994 | Freedman | 324/303 |
| 5,309,098 A | 5/1994 | Coates et al. | 324/303 |
| 5,349,184 A | 9/1994 | Wraight | 250/266 |
| 5,350,925 A | 9/1994 | Watson | 250/269.3 |
| 5,359,324 A | 10/1994 | Clark et al. | 340/854.3 |
| 5,363,041 A | 11/1994 | Sezginer | 324/303 |
| 5,376,884 A | 12/1994 | Sezginer | 324/303 |
| 5,379,216 A | 1/1995 | Head | 364/422 |
| 5,381,092 A | 1/1995 | Freedman | 324/303 |
| 5,387,865 A | 2/1995 | Jerosch-Herold et al. | 324/303 |
| 5,397,989 A | 3/1995 | Spraul et al. | 324/321 |
| 5,412,320 A | 5/1995 | Coates | 324/303 |
| 5,432,446 A | 7/1995 | Macinnis et al. | 324/303 |
| 5,453,692 A | 9/1995 | Takahashi et al. | 324/318 |
| 5,486,761 A | 1/1996 | Sezginer | 324/303 |
| 5,486,762 A | 1/1996 | Freedman et al. | 324/303 |
| 5,497,087 A | 3/1996 | Vinegar et al. | 324/303 |
| 5,498,960 A | 3/1996 | Vinegar et al. | 324/303 |
| 5,517,115 A | 5/1996 | Prammer | 324/303 |
| 5,557,200 A | 9/1996 | Coates | 324/303 |
| 5,557,201 A | 9/1996 | Kleinberg et al. | 324/303 |
| 5,565,775 A | 10/1996 | Stallmach et al. | 324/303 |
| 5,629,623 A | 5/1997 | Sezginer et al. | 324/303 |
| 5,680,043 A | 10/1997 | Hurlimann et al. | 324/303 |
| 5,705,927 A | 1/1998 | Sezginer et al. | 324/303 |
| 5,757,186 A | 5/1998 | Taicher et al. | 324/303 |
| 5,767,674 A | 6/1998 | Griffin et al. | 324/303 |
| 5,796,252 A | 8/1998 | Kleinberg et al. | 324/303 |
| 5,869,755 A | 2/1999 | Ramamoorthy et al. | 73/152.05 |
| 5,914,598 A | 6/1999 | Sezginer et al. | 324/303 |
| 5,923,167 A | 7/1999 | Chang et al. | 324/303 |
| 5,936,405 A | 8/1999 | Prammer et al. | 324/303 |
| 5,977,768 A | 11/1999 | Sezginer et al. | 324/303 |
| 5,992,519 A | 11/1999 | Ramakrishnan et al. | 166/250.15 |
| 6,005,389 A | 12/1999 | Prammer | 324/303 |
| 6,008,646 A | 12/1999 | Griffin et al. | 324/303 |
| 6,049,205 A | 4/2000 | Taicher et al. | 324/303 |

OTHER PUBLICATIONS

Brown et al., "Nuclear Magnetism Logging," Transactions of the American Institute of Mining, Metallurgical, and Petroleum Engineers, vol. 219 (1960), pp. 199–207.

Brownstein et al., "Importance of classical diffusion in NMR studies of water in biological cells," The American Physical Society, vol. 19, No. 6, (1979) pp. 2446–2453.

Cannon et al., "Quantitative NMR Interpretation," Society of Petroleum Engineers, SPE 49010, 1998.

Carr et al., "Effects of Diffusion on Free Precision in Nuclear Magnetic Resonance Experiments," *Physical Review*, vol. 94. No. 3 (May 1, 1954), pp. 630–638.

Chandler et al., "Improved Log Quality with a Dual–Frequency Pulsed NMR Tool," *Society of Petroleum Engineers* (1994) pp. 23–35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Improving the Accuracy of NMR Relaxation Distribution Analysis in Clay–Rich Reservoirs and Core Samples," paper SCA 9702, in 1997 international symposium proceedings: Society of Professional Well Log Analysts, Society of Core Analysts Chapter–at–large, p. 10, 1997.

Chen et al., "Estimation of Hydrocarbon Viscosity with Multiple TE Dual Wait–Time MRIL Logs," Society of Petroleum Engineers, SPE 49009, 1998.

Clavier et al., "Theoretical and Experimental Bases for the Dual–Water Model for Interpretation of Shaly Sands," Society of Petroleum Engineers Journal, 1984, pp. 153–168.

Coates et al., "An Investigation of a New Magnetic Resonance Imaging Log," National SPWLA Convention (Jun. 18, 1991), pp. 1–24.

Coates et al., "Applying NMR Total and Effective Porosity to Formation Evaluation," Society of Petroleum Engineers, Inc., SPE 38736, 1997.

Coates et al., "Core Data and MRIL Show—A New Approach to 'Formation Factor,'" National SPWLA Convention (Jun. 15, 1992), pp. 1–15.

Coates et al., "A New Approach to Improved Log–Derived Permeability," SPWLA Fourteenth Annual Logging Symposium, May 6–9, 1973, pp. 1–27.

Coates et al., "The Magnetic Resonance Imaging Log Characterized by Comparison With Petrophysical Properties and Laboratory Core Data," Society of Petroleum Engineers, SPE 22723, 1991, pp. 627–635.

Dunn et al., "A Method for Inverting NMR Data Sets With Different Signal to Noise Ratios," SPWLA 39th Annual Logging Symposium, May 26–29, 1998.

Edwards et al., "Improved NMR Well Logs From Time–Dependent Echo Filtering," SPWLA 37th Annual Logging Symposium, Jun. 16–19, 1996.

Edwards et al., "Effects of Tool Design and Logging Speed on $T_2$ NMR Log Data," SPWLA 38th Annual Logging Symposium, Jun. 15–18, 1997.

Farrar et al., "Pulse and Fourier Transform NMR Introduction to Theory and Methods," Academic Press (1971) pp. 26–29.

Freedman et al., "Combining NMR and Density Logs for Petrophysical Analysis in Gas–Bearing Formations," SPWLA 39th Annual Logging Symposium, May 26–29, 1998.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Howard et al., "Proton Magnetic Resonance and Pore–Size Variations in Reservoir Sandstones," *Society of Petroleum Engineers* (1990), pp. 733–741.

Hull et al., "Field Examples of Nuclear Magnetism Logging," Journal of Petroleum Technology, 1960, pp. 14–22.

Jackson et al., "Western Gas Sands Project Los Alamos NMR Well Logging Tool Development," Los Alamos National Laboratory (Oct. 1981–Sep. 1982) pp. 1–28.

Jasper A. Jackson, "Nuclear Magnetic Resonance Well Logging," The Log Analyst, Sep.–Oct. , 1984, pp. 16–30.

Kenyon et al., "Pore–Size Distribution and NMR in Microporous Cherty Sandstones," SPWLA Thirtieth Annual Logging Symposium (Jun. 11–14, 1989), pp. 1–24.

Kleinberg et al., "Novel NMR Apparatus for Investigating an External Sample," *Journal of Magnetic Resonance*, (1992) pp. 466–485.

Kleinberg et al., "Nuclear Magnetic Resonance of Rocks: $T_1$ vs. $T_2$," Society of Petroleum Engineers, SPE 26470, 1993, pp. 553–563.

Kleinberg et al., "NMR Properties of Reservoir Fluids," The Log Analyst, Nov.–Dec. 1996, pp. 20–32.

Menger et al., "A New Algorithm for Analysis of NMR Logging Data," Society of Petroleum Engineers, Inc., SPE 49013, 1998.

Miller et al., "Spin Echo Magnetic Resonance Logging: Porosity and Free Fluid Index Determination," *Society of Petroleum Engineers*, SPE 20561 (1990), pp. 321–334.

Morriss et al., "Field Test of an Experimental Pulsed Nuclear Magnetism Tool," SPWLA Annual Logging Symposium (Jun. 13–16, 1993), pp. 1–23.

Morriss et al.,"Hydrocarbon Saturation and Viscosity Estimation from NMR Logging in the Belridge Diatomite," 35th SPWLA Annual Logging Symposium (Jun. 19–22, 1994), pp. 1–24.

Nascimento et al., "Anomalous NMR Responses in Highly Permeable Sandstone Reservoirs: A Case Study," SPWLA 40th Annual Logging Symposium, May 30–Jun. 3, 1999.

Neuman et al., "Applications of Nuclear Magnetism Logging to Formation Evaluation," Journal of Petroleum Technology, vol. 34, (1982) pp. 2853–2862.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195–260.

Prammer et al., "Theory and Operation of a New, Multi–Volume, NMR Logging System," SPWLA 40th Annual Logging Symposium, May 30–Jun. 3, 1999.

Prammer et al., "A New Multiband Generation of NMR Logging Tools," Society of Petroleum Engineers, SPE 49011, 1998.

Prammer et al., "Measurements of Clay–Bound Water and Total Porosity by Magnetic Resonance Logging," Society of Petroleum Engineers, SPE 36522, 1996.

Prammer, M.G., "NMR Pore Size Distributions and Permeability at the Well Site," *Society of Petroleum Engineers*, SPE 28368, (1994) pp. 55–64.

*Schlumberger Technology News —Oilfield Bulletin*, "Fifth Generation Nuclear Magnetic Resonance Logging Tool: A Major Advance in Producibility Measurement Technology," (Jul. 1995) (2 pp.).

*Schlumberger Wireline & Testing*, "Combinable Magnetic Resonance tool reliably indicates water–free production and reveals hard–to–find pay zones," (Jun. 1995).

Setser et al., "Measurement of Remaining Oil Saturation in Northern Michigan Using Nuclear Magnetism Log Data and Pressure Core," Society of Petroleum Engineers, SPE 14276, 1985.

Singer et al., "Fast NMR Logging for Bound Fluid and Permeability," SPWLA 38th Annual Logging Symposium, Jun. 15–18, 1997.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Tang et al., "LP–Zoom, a Linear Prediction Method for Local Spectral Analysis of NMR Signals," Journal of Magnetic Resonance 79, 190–196 (1988).

Waxman et al., "Electrical Conductivities in Oil–Bearing Shaly Sands," *Society of Petroleum Engineers Journal* (1968) pp. 107–122.

FIG.3A — GAS ZONE
FIG.3B — OIL ZONE
FIG.3C — WET ZONE

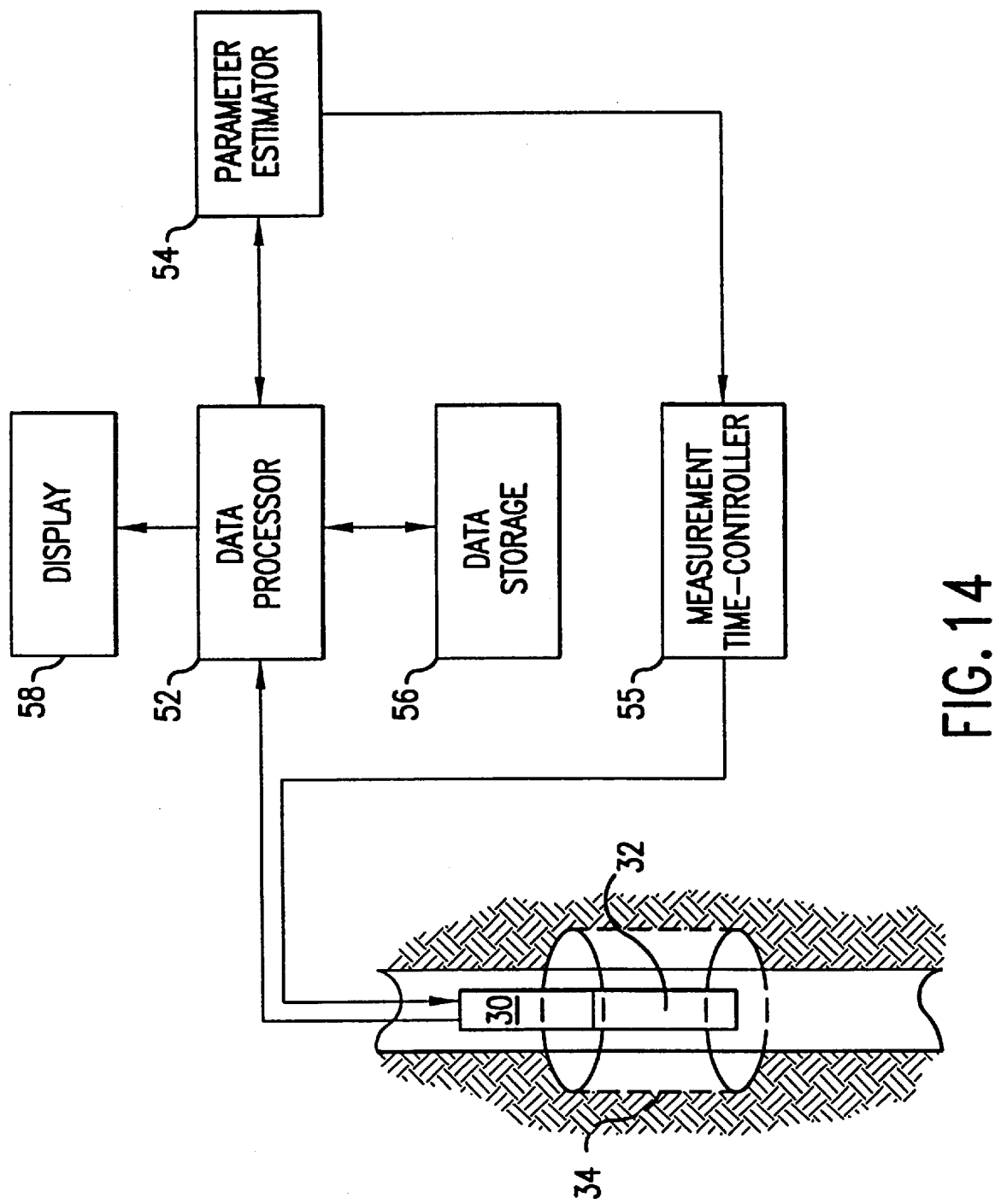

NMR LOGGING APPARATUS AND METHODS FOR FLUID TYPING

Priority of provisional application No. 06/106,259 filed on Oct. 30, 1998, in The United States is claimed under 35 U.S.C. § 119.

FIELD OF THE INVENTION

The present invention relates to nuclear magnetic resonance (NMR) borehole measurements and more particularly to fluid typing based on separation of signals from different fluids using user-adjusted measurement parameters.

BACKGROUND

The ability to differentiate between individual fluid types is one of the main concerns in the examination of the petrophysical properties of a geologic formation. For example, in the search for oil it is important to separate signals due to producible hydrocarbons from the signal contribution of brine, which is a fluid phase of little interest. Extremely valuable is also the capability to distinguish among different fluid types, in particular, among clay-bound water, capillary-bound water, movable water, gas, light oil, medium oil, and heavy oil. However, so far no approach has been advanced to reliably perform such fluid typing in all cases.

In evaluating the hydrocarbon production potential of a subsurface formation, the formation is described in terms of a set of "petrophysical properties." Such properties may include: (1) the lithology or the rock type, e.g., amount of sand, shale, limestone, or more detailed mineralogical description, (2) the porosity or fraction of the rock that is void or pore space, (3) the fluid saturations or fractions of the pore space occupied by oil, water and gas, and others. Various methods exist for performing measurements of petrophysical parameters in a geologic formation. Nuclear magnetic resonance (NMR) logging, which is the focus of this invention, is among the best methods that have been developed for a rapid determination of such parameters, which include formation porosity, composition of the formation fluid, the quantity of movable fluid and permeability, among others. At least in part this is due to the fact that NMR measurements are environmentally safe. Importantly, NMR logs differ from conventional neutron, density, sonic, and resistivity logs in that NMR logs are essentially unaffected by matrix mineralogy, i.e., provide information only on formation fluids. The reason is that NMR signals from the matrix decay too quickly to be detected by the current generation NMR logging tools. However, such tools are capable of directly measuring rock porosity filled with the fluids. Even more important is the unique capability of NMR tools, such as NUMAR's MRIL® tool, to distinguish among different fluid types, in particular, clay-bound water, capillary-bound water, movable water, gas, light oil, medium oil, and heavy oil by applying different sets of user-adjusted measurement parameters.

To better appreciate how NMR logging can be used for fluid signal separation, it is first necessary to briefly examine the type of parameters that can be measured using NMR techniques. NMR logging is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the spin-spin relaxation time $T_2$ (also known as transverse relaxation time), which is an expression of the relaxation due to non-homogeneities in the local magnetic field over the sensing volume of the logging tool. Both relaxation times provide information about the formation porosity, the composition and quantity of the formation fluid, and others.

Another measurement parameter obtained in NMR logging is the diffusion of fluids in the formation. Generally, diffusion refers to the motion of atoms in a gaseous or liquid state due to their thermal energy. Self-diffusion is inversely related to the viscosity of the fluid, which is a parameter of considerable importance in borehole surveys. In a uniform magnetic field, diffusion has little effect on the decay rate of the measured NMR echoes. In a gradient magnetic field, however, diffusion causes atoms to move from their original positions to new ones, which moves also cause these atoms to acquire different phase shifts compared to atoms that did not move. This effect contributes to a faster rate of relaxation in a gradient magnetic field.

NMR measurements of these and other parameters of the geologic formation can be done using, for example, the centralized MRIL® tool made by NUMAR, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Millen, Granot and Bouton, SPE 20561, 65th Annual Technical Conference of the SPE, New Orleans, La., Sept. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sept. 25–28, 1994. Details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200 and 5,696,448, all of which are commonly owned by the assignee of the present invention. The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992. The content of the above patents is hereby expressly incorporated by reference; the content of the publications is incorporated by reference for background.

It has been observed that the mechanisms determining the measured values of $T_1$, $T_2$ and diffusion depend on the molecular dynamics of the formation being tested and on the types of fluids present. Thus, in bulk volume liquids, which typically are found in large pores of the formation, molecular dynamics is a function of both molecular size and inter-molecular interactions, which are different for each fluid. Water, gas and different types of oil each have different $T_1$, $T_2$ and diffusivity values. On the other hand, molecular dynamics in a heterogeneous media, such as a porous solid that contains liquid in its pores, differs significantly from the dynamics of the bulk liquid, and generally depends on the mechanism of interaction between the liquid and the pores of the solid media. It will thus be appreciated that a correct interpretation of the measured signals can provide valuable information relating to the types of fluids involved, the structure of the formation and other well-logging parameters of interest.

It should be clear that the quality of the fluid typing depends on the magnitudes of the contrasts between measurement signals from different fluid types. Generally, as the contrasts increase, the quality of the typing improves. Table 1 below shows the ranges of the characteristic parameters for brine, gas, and oil measured by an MRIL®-C tool under typical reservoir conditions (i.e., pressure (P) from 2,000 to 10,000 psi, and temperature (T) from 100 to 350° F.). Table 2 shows typical parameter values for a Gulf of Mexico sandstone reservoir. The information in the tables clearly reveals a broad distribution for $T_1$, $T_2$, D, and hydrogen index (HI) that is used in accordance with the present invention in fluid typing.

TABLE 1

Ranges of the characteristic parameters of water, gas, and oil measured with an MRIL ®-C tool under typical reservoir conditions

|  | Free Water | Bound Water | Gas | Oil |
| --- | --- | --- | --- | --- |
| Hydrogen Index (HI) | ~1 | ~1 | <1 | <~1 |
| Diffusion (D) | medium | very low | very high | low |
| Relaxation Time ($T_1$) | medium | short | long | long |
| Relaxation Time ($T_2$) | medium | short | short | long |

TABLE 2

Typical values of characteristic parameters for fluids in a Gulf of Mexico sandstone reservoir

|  | $T_1$ (ms) | $T_2$ (ms) | HI | $D_0 \times 10^{-5}$ cm$^2$/s | $D_0 T_1$ cm$^2$ |
| --- | --- | --- | --- | --- | --- |
| Brine | 1–500 | 0.67–200 | 1 | 7.7 | 0.0077–4.0 |
| Oil | 5,000 | 460 | 1 | 7.9 | 40 |
| Gas | 4,400 | 40 | 0.38 | 100 | 440 |

Despite the existing contrasts, a problem encountered in standard NMR measurements is that in some cases signals from different fluid phases cannot be fully separated. For example, NMR signals due to brine, which is of no interest to oil production, cannot always be separated from signals due to producible hydrocarbons. The reason is that for a particular measurement parameter there is an overlap in the ranges of the measured signals from these fluids.

Several methods for acquiring and processing gradient NMR well log data have been proposed recently that enable the separation of different fluid types. These separation methods are based primarily on the existence of a $T_1$ contrast and a diffusion contrast in NMR measurements of different fluid types. Specifically, a $T_1$ contrast is due to the fact that light hydrocarbons have long $T_1$ times, roughly 1 to 3 seconds, whereas $T_1$ values longer than 1 second are unusual for water-wet rocks. In fact, typical $T_1$'s are much shorter than 1 sec, due to the typical pore sizes encountered in sedimentary rocks, providing an even better contrast.

Diffusion in gradient magnetic fields provides a separate contrast mechanism applicable to $T_2$ measurements that can be used to further separate the long $T_1$ signal discussed above into its gas and oil components. In particular, at reservoir conditions the self-diffusion coefficient $D_0$ of gases, such as methane, is at least 50 times larger than that of water and light oil, which leads to proportionately shorter $T_2$ relaxation times associated with the gas. Since diffusion has no effect on the $T_1$ measurements, the resulting diffusion contrast can be used to separate oil from gas.

The $T_1$ and diffusion contrast mechanisms have been used to detect gas and separate fluid phases in what is known as the differential spectrum method (DSM) proposed first in 1995. There are several problems associated with prior art methods, such as DSM. For example, generally DSM requires a logging pass associated with relatively long wait times ($T_W$ approximately 10 sec) so that DSM-based logging is relatively slow. Further, the required $T_1$ contrast may disappear in wells drilled with water-based mud, even if the reservoir contains light hydrocarbons. This can happen because water from the mud invades the big pores first, pushing out the oil and thus adding longer $T_2$'s to the measurement spectrum. In such cases, DSM or standard NMR time domain analysis (TDA) methods have limited use either because there is no separation in the $T_2$ domain, or because the two phases are too close and can not be picked robustly. Separation problems similar to the one described above can also occur in carbonate rocks. In carbonates an overlap between the brine and hydrocarbons phases is likely because the surface relaxivity in carbonates is approximately ⅓ that of sandstones. In other words, for the same pore size, the surface relaxation in carbonates is about 3 times longer than that for a sandstone, such weak surface relaxation causing an overlap between the observable fluid phases. Additional problem for carbonates is the presence of vugs. Water bearing vugs, because of their large pore sizes, have long $T_2$'s and can easily be interpreted as oil by prior art techniques. No single technique seems to solve these and other problems encountered in standard logging practice.

It is apparent, therefore, that there is a need for a flexible apparatus and methods, using different contrast mechanisms, in which these and other problems associated with fluid typing in the prior art are obviated.

SUMMARY OF THE INVENTION

The present invention is based on using a combination of several different contrast mechanisms in NMR fluid typing measurements of a geologic formation. To this end, in accordance with the present invention, dependent on the specifics of the geologic formation the measurement tool uses different sets of NMR measurement parameters so as to select the optimum contrast mechanism for fluid typing. The contrast mechanisms used in a preferred embodiment include $T_1$, $T_2$, D, HI, and viscosity η contrasts, which are fundamental to fluid typing. In a preferred embodiment, the present invention uses Numar Corporation's MRIL® tool because of its capability to make multi-contrast measurements. Appropriate selection of pulse sequences, such as CPMG, and acquisition parameters, such as pulse waiting time ($T_W$) and echo spacing time (TE), allows the acquisition of weighted spin echo data with different contrasts.

In particular, in accordance with a preferred embodiment, a method for fluid typing of a geological environment is disclosed, using nuclear magnetic resonance (NMR) measurements. The method comprises: determining a set of parameters for a gradient NMR measurement, obtaining a pulsed NMR log using the determined set of parameters; and selecting from the NMR log an optimum contrast mechanism and corresponding measurement parameters for fluid typing of the geological environment. In a preferred embodiment, the set of determined parameters comprises the interecho spacing TE of a pulsed NMR sequence, the magnetic field gradient G and the wait time $T_w$ of the NMR measurement. Further, in a preferred embodiment, the optimum contrast mechanism used in the method is based on diffusion, relaxation or hydrogen index contrast.

In another aspect of this invention, a method for fluid typing of a geological environment is disclosed using nuclear magnetic resonance (NMR) measurements, where the method comprises: conducting a first NMR measurement using a first predetermined set of measurement parameters; comparing the first NMR measurement results to a predetermined set of criteria applicable for different fluid types to estimate candidate types of fluids that may have produced the first NMR measurement results; selecting an appropriate type of contrast mechanism and a corresponding second set of measurement parameters for the estimated types of fluids; and conducting a second NMR measurement using the second set of parameters to increase the accuracy of the fluid typing determination in case the second set of parameters is different from said first set of parameters. In a preferred embodiment, the first and the second set of parameters correspond to one or more of the DSM, EDM, SSM, TPM, and ICAM fluid typing methods.

In another aspect, the present invention is directed to a computer storage medium storing a software program to be executed on a computer, comprising: a first software application for capturing NMR data concerning a first measurement; a second software application, for comparing the first measurement data to pre-set rules determining the optimum contrast mechanism for use in the environment; and a third software application, for providing a predetermined set of measurement parameters according to the determined optimum contrast mechanism.

In another aspect, the present invention is an apparatus for fluid typing of a geological environment using nuclear magnetic resonance (NMR) measurements comprising: a logging tool capable of conducting NMR measurements in a borehole; data storage for storing NMR log data corresponding to one or more NMR measurements each measurement using a predetermined set of measurement parameters; a computer processor configured to execute a software application program for selecting from NMR log data an optimum contrast mechanism and corresponding measurement parameters for fluid typing of the geological environment; and a measurement cycle controller providing control signals to the logging tool for conducting NMR measurements based on input from said processor. In a preferred embodiment, the apparatus comprises a display for indicating the selection of measurement parameters to a human operator, and the logging tool has a dual wait-time sequencing capability.

BRIEF DESCRIPTION OF THE DRAWINGS

The present invention will be understood and appreciated more fully from the following detailed description taken in conjunction with the drawings in which:

FIG. 14 is a block diagram of the apparatus in accordance with a preferred embodiment, which shows individual block components for controlling data collection, processing the collected data and displaying the measurement results.

DETAILED DESCRIPTION OF THE PREFERRED EMBODIMENTS

A. The System

Figure 13:
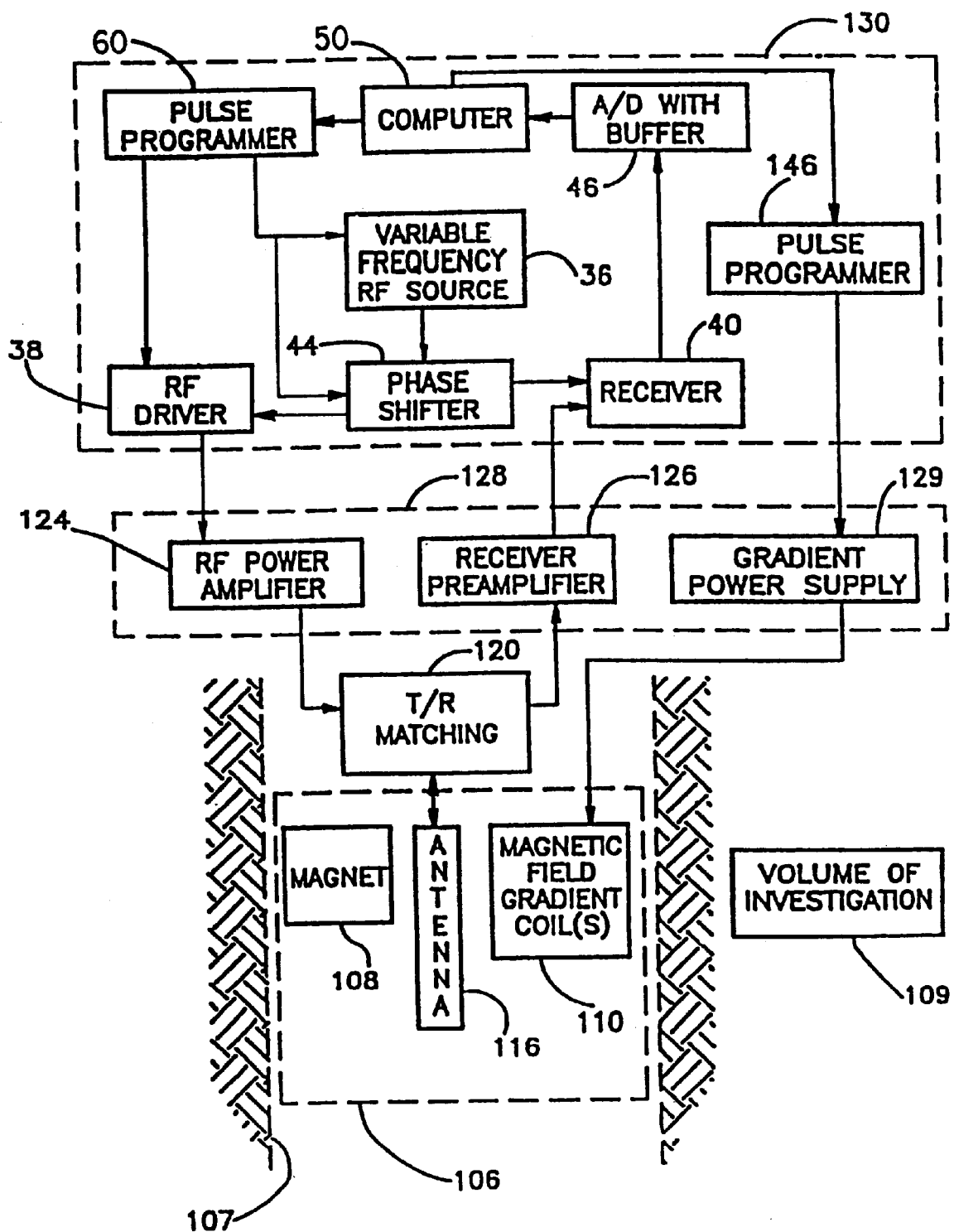
FIG. 13 is a partially pictorial, partially block diagram illustration of an apparatus for obtaining nuclear magnetic resonance (NMR) measurements in accordance with a preferred embodiment of the present invention.

Reference is first made to FIG. 13, which illustrates an apparatus constructed and operative in accordance with a specific embodiment of the present invention for obtaining multi-contrast nuclear magnetic resonance (NMR) measurements. The apparatus includes a first portion 106, which is arranged to be lowered into a borehole 107 in order to examine the nature of materials in the vicinity of the borehole.

The first portion 106 comprises a magnet or a plurality of magnets 108, which preferably generate a substantially uniform static magnetic field in a volume of investigation 109 extending in the formation surrounding the borehole. The first portion 106 also comprises an RF antenna coil 116 which produces an RF magnetic field at the volume of investigation 109.

A magnetic field gradient coil, or plurality of coils, 110 generates a magnetic field gradient at the volume of investigation 109. This additional contribution to the magnetic field, which is essential for the fluid typing methods of the present invention using diffusion, has a field direction preferably collinear with the substantially uniform field and has a substantially uniform magnetic field gradient. The magnetic field gradient may or may not be pulsed, i.e., switched on and off by switching the dc current flowing through the coil or coils 110. The magnet or magnets 108, antenna 116 and the gradient coil 110 constituting portion 106 are also referred to as a probe.

The antenna together with a transmitter/receiver (T/R) matching circuit 120, which typically includes a resonance capacitor, a T/R switch and both to-transmitter and to-receiver matching circuitry, are coupled to an RF power amplifier 124 and a receiver preamplifier 126. A power supply 129 provides the dc current required for the magnetic field gradient generating coils 1 10. All the elements described above are normally contained in a housing 128 which is passed through the borehole. Alternatively, some of the above elements may be located above ground.

Indicated in a block 130 is control circuitry for the logging apparatus including a computer 50, which is connected to a pulse programmer 60 that controls the operation of a variable frequency RF source 36 as well as an RF driver 38. RF driver 38 also receives input from the variable frequency source 36 through a phase shifter 44, and outputs to RF power amplifier 124.

The output of RF receiver amplifier 126 is supplied to an RF receiver 40 which receives an input from a phase shifter 44. Phase shifter 44 receives an input from variable frequency RF source 36. Receiver 40 outputs via an A/D converter with a buffer 46 to computer 50 for providing desired well logging output data for further use and analysis. Pulse programmer 146 controls the gradient coil power supply 129 enabling and disabling the flow of current, and hence the generation of static or pulsed field gradients, according to the commands of the computer 50. Some or all of the elements described hereinabove as being disposed in an above-ground housing, may instead be disposed below ground.

FIG. 13 depicts one embodiment of the apparatus used in accordance with the present invention. In an alternative preferred embodiment, in accordance with the present invention, various models of the MRIL® tool to Numar Corporation, or other tools known in the art, can be used instead. FIG. 14 is a block diagram of a generic system used in accordance with the present invention, and shows individual block components for controlling data collection, processing the collected data and displaying the measurement results. In FIG. 14 the tool's electronic section 30 comprises a probe controller and pulse echo detection electronics. The output signal from the detection electronics is processed by data processor 52 to analyze the relaxation characteristics of the material being investigated. The output of the data processor 52 is provided to the parameter estimator 54. In accordance with the present invention, data processor 52 operates in conjunction with parameter estimator 54 to determine an optimal contrast mechanism to be used for fluid typing in the particular borehole environment. As discussed in more detail below, several different contrast mechanisms can be used in a preferred embodiment. The selection of a suitable contrast mechanism by the data processor is then translated into the selection of a corresponding data acquisition technique, and/or a different set of measurement parameters.

Dependent on the selected data acquisition technique, measurement cycle controller 55 provides an appropriate control signal to the probe. The processed data from the log measurement is stored in data storage 56. Data processor 52 is connected to display 58, which is capable of providing a graphical display of one or more measurement parameters, possibly superimposed on display data from data storage 56. Accordingly, the selection of the optimal contrast mechanism for a particular measurement can be done by a human operator, or automatically, pursuant to a pre-set number of rules.

The components of the system of the present invention shown in FIG. 14 can be implemented in hardware or software, or any combination thereof suitable for practical purposes. Details of the structure, the operation and the use of logging tools, as illustrated in FIGS. 13 and 14 are also discussed, for example, in the description of the MRIL® tool to Numar Corporation, and in U.S. Pat. Nos. 4,717,876; 4,717,877; 4,717,878; 5,212,447; 5,280,243; 5,309,098; 5,412,320; 5,517,115, 5,557,200 and 5,696,448, the contents of which are incorporated herein for all purposes.

In a preferred embodiment of the present invention the selection of the optimum contrast mechanism for use in fluid typing in a particular borehole environment is done by comparing results from a first NMR measurement to a predetermined set of criteria applicable for different fluid types. The criteria used in a preferred embodiment are based on the theoretical models, which are discussed in further detail next, as well as other types of measurements, prior experience, and other available information. At this stage, the apparatus of this invention determines broadly the type of fluids that may have produced the first NMR measurement results and then, if necessary, selects the appropriate type of contrast mechanism and corresponding measurement parameters to possibly increase the accuracy of the fluid typing determination. In some instances, this may lead to a second measurement pass with a different set of measurement parameters. In a preferred embodiment, the selection criteria can be implemented in software, using a rule based (i.e., if. . . . then) approach in accordance with the models discussed next. Preferably, the software used in the present invention is stored in a computer storage medium for execution on a computer, such as data processor 52.

In a specific embodiment, the fluid typing program of the present invention comprises: a first software application for capturing NMR data concerning a first measurement; a second software application, for comparing the first measurement data to pre-set rules determining the optimum contrast mechanism for use in the environment; and a third software application, for providing a predetermined set of measurement parameters according to the determined optimum contrast mechanism.

B. The Methods

In accordance with the present invention, fluid typing for detecting and quantitatively measuring volumes occupied by brine, gas, and oil is done using several different methods, which are based on nuclear magnetic resonance (NMR) logging data. In particular, the methods of the present invention include Differential Spectrum Method (DSM), Enhanced Diffusion Method (EDM), Shifted Spectrum Method (SSM) in transverse relaxation time ($T_2$) domain or in spin-echo time domain (i.e., Time Domain Analysis; TDA), Total Porosity Measurement (TPM), and Injecting Contrast Agent Method (ICAM). Generally, DSM is used in accordance with the present invention for gas and light oil; EDM is used for medium oil; SSM for gas and oil; TPM for bound water, including clay-bound water and capillary-bound water and movable fluids; and ICAM for residual oil saturation (ROS) measurements. Each of these methods and the associated contrast mechanisms are discussed in more detail next. A brief summary of the contrast mechanisms used in accordance with the present invention is presented next to help understand the individual fluid typing methods.
. Contrast Mechanisms
. (a) The HI Contrast The HI contrast associated with a particular molecule is a function of the molecule's mass density, as well as the number of hydrogen nuclei (protons) in the molecule. For a pure hydrocarbon, it has been shown (see, e.g., Kleinberg, R. L., and Vinegar, H. J.: "NMR Properties of Reservoir Fluids," The Log Analyst (November–December, 1996) that $$HI = \rho * n_H / 0.11 * MW \tag{1}$$

where $\rho$, MW, and $n_H$ are mass density, molecular weight, and number of hydrogen atoms in the molecule, respectively. The above Eq. (1) has been modified the equation for oil:

$$HI = \rho * [R/(12.011 + 1.008\,R)]/0.11 \tag{2}$$

where R is the ratio of hydrogen atoms to carbon atoms in the oil. For additional information, see, for example, Lo, S. W., et al.: "Some Exceptions to Default NMR Rock and Fluid Properties," paper FF presented at the 39$^{th}$ Annual SPWLA Logging Symposium, Keystone, Colorado, U.S.A., May 26–29, 1998, which is incorporated herein for backgound.

(b) Relaxation Times Contrasts

The contrasts of the relaxation times ($T_1$ and $T_2$) result from different relaxation mechanisms that dominate in the fluids. The $T_2$ of a fluid in a rock has been expressed as $$1/T_2 = 1/T_{2S} + 1/T_{2B} + 1/T_{2D} \tag{3}$$

where $T_{2S}$ is the contribution from the surfaces of the pore wall and the clays, $T_{2B}$ is the contribution from the bulk fluid, and $T_{2D}$ is a term related to molecular diffusion in a magnetic gradient field. This gradient is either an external gradient, such as the lineal gradient produced by an MRIL® tool, or an internal gradient from clays. Bulk relaxation ($T_{2B}$) is from either the magnetic dipole-dipole (DD) interaction for liquids or the spin-rotation (SR) interaction for gases. For a liquid in a low magnetic field from the MRIL® tool, the $T_{2B}$ component is given by $$(1/T_2)_{DD} \sim \gamma^4 * \tau_c * r^{-6} \tag{4}$$

where $\gamma$ is the proton gyromagnetic ratio, $\tau_c$ is the rotational correlation time, and r is the distance between the spins.

For a gas, the $T_{2B}$ component is given by the expression $$(1/T_2)_{SR} \sim I * T * C_{eff}^2 * \tau_J \tag{5}$$

where I is the moment of inertia of the molecule, $C_{eff}$ is the effective spin-rotational coupling constant, and $\tau_J$ is the angular-momentum correlation time. For background information, see Bloembergen, N., Purcell, E. M., and Pound, R. V.: "Relaxation Effects in Nuclear Magnetic Resonance Absorption," *Physical Review*, (1948) 73, 679.

The bulk relaxation of oil is a main contribution to $T_2$ for a water-wet reservoir. The relationship between the $T_2$ of an oil and the viscosity of the oil has been expressed as $$T_2 = 1.2 * (T/298 * \eta)^{0.9} \tag{6}$$

See Morriss, C. E., et al.: "Hydrocarbon Saturation and Viscosity Estimation from NMR Logging in the Belridge Diatomite," *The Log Analyst* (March–April, 1997). Equation 6 is valid only for dead oil and for oil with uni-exponential decay. For oil having a distribution of $T_2$ values, $T_2$ in the equation should be considered as the geometric mean of the distribution.

The surface term $T_{2S}$ in Eq. (3) above is given by the expression:

$$T_{2S} = (\rho_2 * S/V_p)^{-1} \tag{7}$$

where $\rho_2$ is the NMR surface relaxivity for $T_2$, $V_p$ is the pore volume, and S is the surface of the pore or clay. For a sphere, $S/V_p$ is $3/r$, and r is the pore radius. In a fast-diffusion case, this equation sets up a relationship between the $T_2$ distribution and a pore size distribution. For background, see, e.g. Kenyon, W. E.: "Petrophysical Principles of Applications of NMR Logging," *The Log Analyst* (March–April 1997).

When using a Carr-Purcell-Meiboom-Gill (CPMG) pulse sequence and existing a linear gradient G, the diffusion term in Eq. (3) is given by $$T_{2D} = 12/[D * (\gamma * TE * G)^2] \tag{8}$$

where D is a self-diffusion coefficient, and TE is an echo-spacing time.

The $T_{2D}$ term shown in Eq. (8) is the only term in Eq. (3) that can be controlled by the user of an MRIL® tool. In particular, in accordance with the present invention, the user can change $T_{2D}$ by adjusting the TE and G parameters of the tool. Details concerning the modification of these parameters are discussed in several patents to the assignee of the present application, which are incorporated by reference herein.

In accordance with the present invention, in a water-wet reservoir, the $T_2$ parameter of the brine phase is generally determined by $T_{2S}$; the $T_2$ of oil is obtained from $T_{2B}$, and the $T_2$ of gas is approximately equal to $T_{2D}$.

The $T_1$ of a formation fluid is described by $$1/T_1 = 1/T_{1S} + 1/T_{1B} \tag{9}$$

A diffusion term is not included in this equation because diffusion involves a spin dephasing process, which is a $T_2$ process.

The equations for $T_{1B}$ for bulk liquids and gas in the low magnetic field are analogous to Eq. 4 and 5 for $T_{2B}$. $T_{1S}$ is the surface relaxation contribution, and is given by $$T_{1S} = (\rho_1 * S/V_p)^{-1} \tag{10}$$

where $\rho_1$ is the surface relaxivity for $T_1$. For a gas, $T_1$ is generally controlled by the $T_{1B}$ component. As known in the art, $T_1$ can also be described by the following equation:

$$T_1 = 2.5 * 10^3 * \rho / T^{1.17} \tag{11}$$

where $T_1$ is in seconds, the density $\rho$ is in g/cm$^3$, and the temperature (T) in degrees Kelvin.

This equation reveals that temperature and pressure (the density term in the equation is related to pressure) have opposite effects on $T_1$.

$T_1$ of gas is very long because of the small angular-momentum correlation time ($\tau_J$) of gas. In a water-wet reservoir, $T_1$ of oil is obtained from bulk relaxation and can be written as $$T_1 = 1.2 * T/298 * \eta \tag{12}$$

$T_1$ of brine is determined by the surface term. The $T_1/T_2$ ratio of brine ranges from approximately 1 to 1.5. For additional background, see for example Kleinberg, R. L., et al.: "Nuclear Magnetic Resonance of Rocks: $T_1$ vs. $T_2$," paper SPE 26470 presented the 1993 SPE Annual Technical Conference and Exhibition, Houston, Tex., U.S.A., Oct. 3≠6, 1993.

(c) Diffusion Contrast

It is known in the art that the contrast of D generally depends on molecular mobility. Hence, D is a function of temperature T, pressure P, and the environment, in which the diffusion molecule exists. The diffusion relaxation mechanism depends on the diffusion of molecules in magnetic field gradients, such as those generated by the MRIL® tool. Ordinarily, diffusion is a predominant relaxation mechanism only for gas. For the fast-diffusion case, D of gas is given by the known expression $$D_g = 8.5 * 10^{-7} * T^{0.9}/\rho \tag{13}$$

D of oil is $$D_o = 1.3 \, T/298 * \eta \tag{14}$$

and D of movable water (mw) is $$D_{mw} = 1.2 \, T/298 * \eta \tag{15}$$

Generally, gas and water each have only one value of D for a certain T and P. However, an oil has a distribution of D because of the many different types of molecules in the oil. In oil, the $D_o$ in Eq. (14) should be considered, in accordance with the present invention, as the value of the geometric mean of this distribution.

1. The Differential Spectrum Method (DSM)

In principle, DSM is a $T_1$-contrast weighed method. The information in Tables 1 and 2 shows that gas and light oil each have a $T_1$ much larger than that of brine. Hence, in accordance with the present invention, the method is used for typing gas and light oil. For a detailed discussion of aspects of this method, the reader is directed to U.S. Pat. Nos. 5,497,087 and 5,498,960 to Vinegar et al., and to co-pending patent applications Ser. Nos. 08/822,567 and 09/270,616 to the assignee of the present application, which are hereby incorporated by reference.

Magnetization in a CPMG spin echo train for a reservoir having three phase (brine, gas, oil) can be described by $$M(n*TE)[1-\exp(-T_w/T_{1b})]*\exp(-n*TE/T_{2Ab})+HI_g*[1-\exp(-T_w/T_{1g})]*\exp(-n*TE/T_{2Ag})+HI_o*[1-\exp(-T_w/T_{1o})]*\exp(-n*TE/T_{2Ao})$$ (16)

where A, b, g, and o in the subscripts represent apparent, brine, gas, and oil, respectively, and n is echo number. According to this equation and the values in Table 2, the brine phase can be eliminated and the oil and gas phases can be still left in a differential echo train from two CPMG acquisition data if $T_{W1} \gg T_{1b}$ and $TW_2 \gg T_{1b}$ but $T_{W1} > TW_2 \sim T_{1g}$ and $T_{W1} > T_{W2} \sim T_{1o}$.

For a Gulf of Mexico sandstone reservoir, it has been suggested that optimum $T_{W1}$ and $TW_2$ values are 1 second and 8 seconds, respectively. This experimental result has been suggested in, for example, Akkurt, R., Prammer, M. G., and Moore, M. A.: "Selection of Optimal Acquisition Parameters for MRIL Logs," *The Log Analyst* (November–December 1996). When such $T_W$s are used in CPMG pulse sequences, the brine signal can be eliminated by taking the difference of the two echo trains. The resulting hydrocarbon signals in the difference can be still large. The remaining oil and gas signals are very well separated from each other in a $T_2$ spectrum.

Figure 1A:
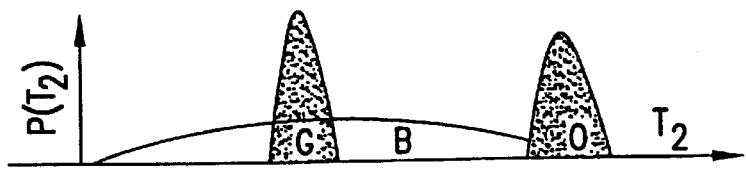
FIG. 1 illustrates the principles used for fluid typing in the Differential Spectrum Method (DSM) of the present invention.
Figure 1B:
Figure 1C:

FIG. 1 illustrates the principle of the DSM used for fluid typing in accordance with the present invention. In FIG. 1(a), all three phases have a filly polarized $T_2$ spectrum at the long $T_{W1}$. In FIG. 1(b), the brine is still filly polarized, but the oil and gas are partially polarized at the $TW_2$. FIG. 1(c) is the difference between the spectra in FIGS. 1(a) and 1(b), and shows the reduced and separated oil and gas signals.

DSM Data Acquisition and Data Processing

The data needed for DSM processing in accordance with the present invention consists of two spin echo trains acquired with two different $T_W$ CPMG pulse sequences. The TW's that are used must satisfy the following conditions: $T_{W1} \gg T_{W2} \gg T_{1b}$, $T_{W2} < \sim T_{1o}$, $T_{W2} < \sim T_{1g}$, $T_{W1} \sim 2T_{1o}$, and $T_{W1} \sim 2T_{1g}$. The TE parameter is chosen in a preferred embodiment to be approximately 1 ms to limit diffusion influences on $T_2$. The number of echos depends on the longest $T_2$ ($T_{2L}$) in the formation, and is chosen in a preferred embodiment to satisfy the condition $(n*TE) \geq T_{2L}$.

As known in the art, in the DSM, data is processed either in a $T_2$ domain or in a time domain. The processing done in a time domain is referred to as a time domain analysis (TDA).

In accordance with the present invention, processing in the $T_2$ domain analysis involves inverting two spin echo trains to two $T_2$ spectra and then subtracting one spectrum from the other. The process is as illustrated in FIG. 1. The inversion algorithm used in a preferred embodiment is known in the art and is discussed, for example in Prammer, M. G.: "NMR Pore Size Distributions and Permeability at the Well Site," paper SPE 28368 presented at the 1994 SPE Annual Technical Conference and Exhibition, New Orleans, La., U.S.A., Sep. 25–28, 1994.

In accordance with the present invention, TDA processing method is preferred to $T_2$-domain processing for detecting gas. The first step in the TDA processing method is to obtain the echo difference from two $T_W$ spin echo trains. Careful $T_W$ selection ensures that the echo difference contains only gas and light-oil signals. In a preferred embodiment, two matched filters are built based on the $T_1$s and the $T_2$s parameters of the oil and the gas:

$$f(t)_o = [\exp(-T_{W1}/T_{1o}) - \exp(-T_{W2}/T_{1o})]*\exp(-t/T_{2o})$$ (17)

and $$f(t)_g = HI_g*[\exp(-T_{W1}/T_{1g}) - \exp(-T_{W2}/T_{1g})]*\exp(-t/T_{2g})$$ (18)

Use of these filters on the echo difference d(t) allows oil-filled porosity (PO) and gas-filled porosity ($P_g$) to be obtained through the matrix equation $$[f(t)_o \; f(t)_g]*[P_o P_g]^{-1} = d(t)$$ (19)

For a more detailed description of the method, the reader is directed to U.S. patent application Ser. No. 08/822,567 to the assignee of the present application, which is incorporated herein for all purposes. The oil and gas porosities obtained through Eq. 19 are more robust than those from $T_2$ domain analysis, which usually uses more than ten $T_2$ values (bins) to obtain ten corresponding porosity solutions.

Figure 2:
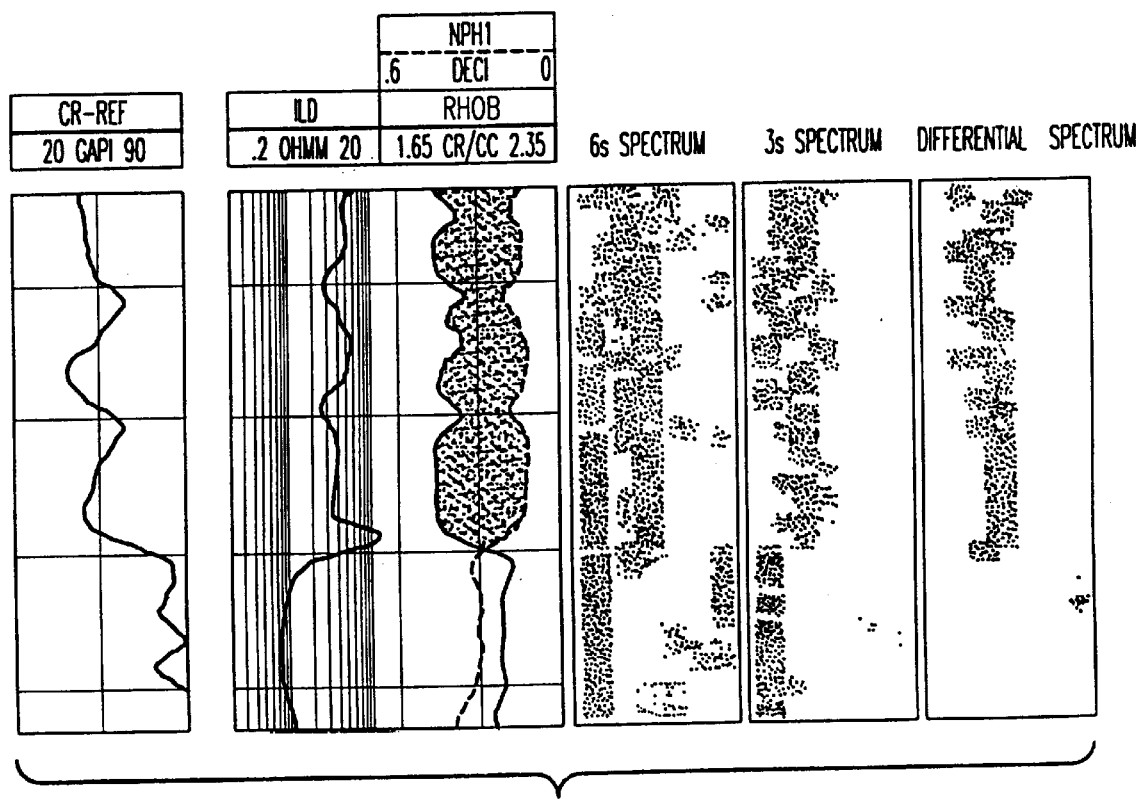
FIG. 2 shows log data and DSM data obtained through $T_2$-domain processing.

In accordance with the present invention, DSM can be used for determining gas volume. See Akkurt et al. "NMR Logging of Natural Gas Reservoirs," Paper N presented at the 36th Annual SPWLA Logging Symposium, Paris, France, Jun. 26–29, 1995, which reported using data from a gradient-based MRIL®-C logging tool, to identify the gas phase in a Gulf of Mexico sandstone reservoir. FIG. 2 shows some of the log data and some of the DSM data obtained through $T_2$-domain processing. The first three tracks (from the left) contain the gamma ray (GR), induction resistivity, and neutron and density logs, respectively. The $T_2$ distributions (spectra) for $T_W$=6 and 3 seconds are displayed in Tracks 4 and 5, and the difference of the two $T_2$ spectra (differential spectrum) is shown in Track 6. The signals in the differential spectrum range from approximately from 32 to 64 ms, which is in the range of gas signal for this tool with acquisition parameter (TE) used and formation temperature that was encountered. All information indicates a gas-bearing zone in the top section of this presentation.

In accordance with the present invention, the $T_W$ selections must be optimized for the specific case. For example, it was determined that the 3 and 6 seconds in the case illustrated above must be replaced with data obtained with $T_W$ values of 8 seconds and 1 seconds for better results for gas detection in the Gulf of Mexico.

Generally, $T_2$ domain analysis on DSM data is not sensitive to the gas signal because the signal is weak and is usually suppressed in the bound water region of a $T_2$ spectrum. TDA has been applied on DSM data from a highly laminated Gulf of Mexico turbidite invaded with synthetic oil filtrate. It has been determined that the conventional $T_2$ domain analysis did not clearly detect the gas signal. However, TDA did show unambiguously both heavy filtrate invasion and the presence of gas where gas saturation was very low.

Figure 3:
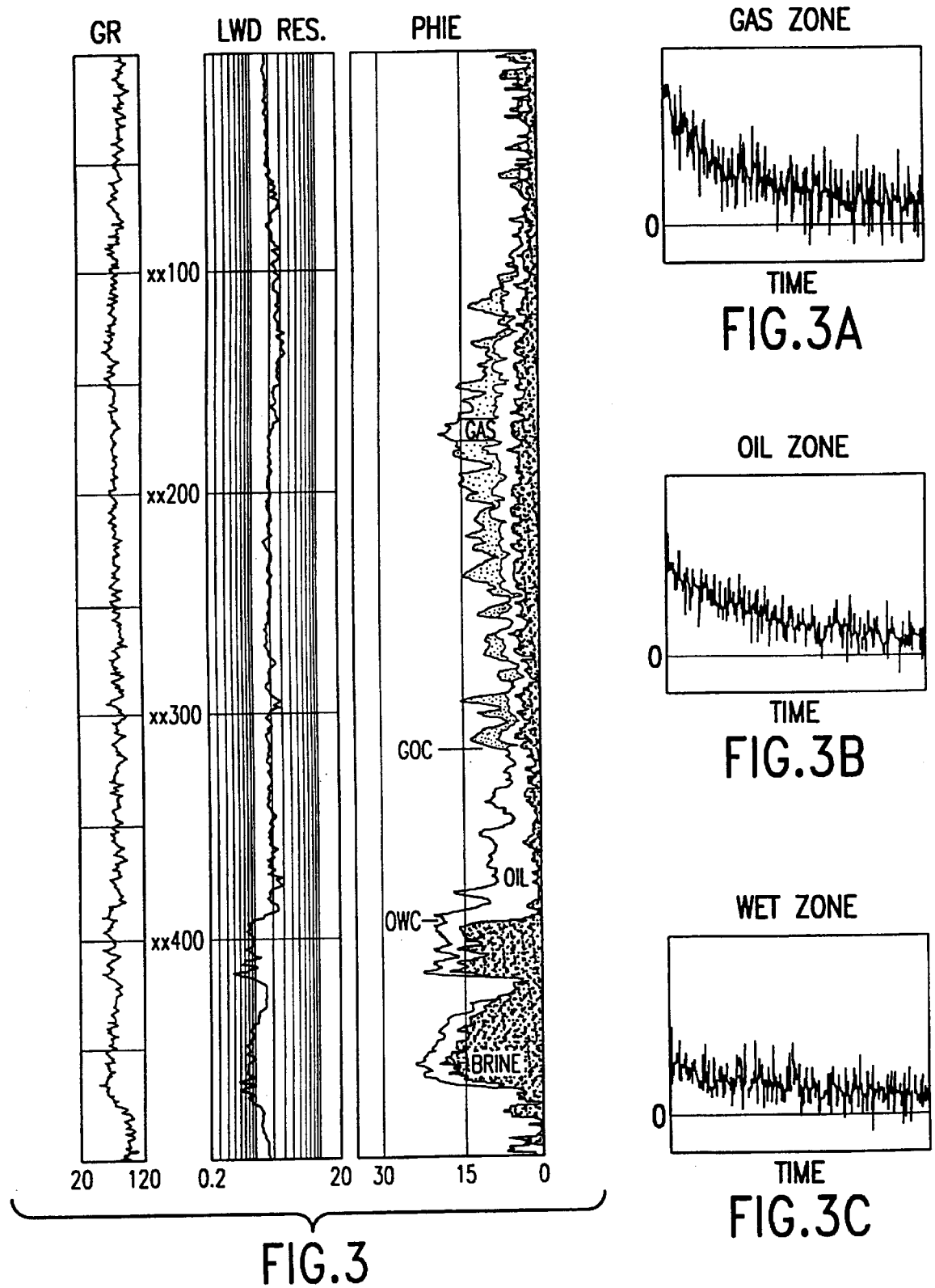
FIG. 3 is an example of using Time Domain Analysis (TDA) of DSM data to find gas, oil, and water-wet zones.

FIG. 3 is an example of using TDA of DSM data to find gas, oil, and water-wet zones in accordance with a specific embodiment of the present invention. In this figure, the first two tracks of the log present logging-while-drilling (LWD) gamma ray and resistivity data, and the third track plots effective porosity obtained by TDA. The gas/oil contact (GOC) and oil/water contact (OWC) were identified by TDA. The echo difference for the gas, the oil, and the brine zone are shown in FIGS. 3(a), 3(b), and 3(c), respectively. The echoes in 3(a) and 3(b) were fitted by the matched filters shown as Eqs. 17 and 18 for the porosities occupied by the gas and the oil.

Because the DSM requires a large $T_1$ contrast, a large diffusion contrast, and a good signal-to-noise ratio (S/N), viable candidates for DSM applications are gas and light-oil reservoirs. In accordance with the present invention, the bulk viscosity of the reservoir oil should preferably be less than about 1 cp, and the apparent gas porosity should be greater than about 1 porosity unit (p.u.) for optimal results.

2. The Enhanced Diffusion Method (EDM)

In accordance with the present invention, the EDM is used for typing medium oil. In principle, the EDM uses diffusion contrast for determining the porosity occupied by a medium oil (i.e., 1 cp<η<50 cp). According to Eq. 3, $T_2$ is smaller than each of $T_{2B}$, $T_{2S}$, and $T_{2D}$. In accordance with the present invention, the parameters G and TE of the measurement device can be adjusted to make $T_{2D}$ a small value for any fluid phase. Through such an adjustment, an upper bound for the $T_2$ spectrum of any phase can be established. Because $T_{2D}$ depends on D, which is a function of temperature and phase, the upper bound shifts according to the phase. For example, at 200° F., the values of D for brine, gas, and 10 cp oil are $7.7 \times 10^{-5}$, $100 \times 10^{-5}$, and $0.1598 \times 10^{-5}$ cm²/s, respectively. If G=18 gauss/cm and TE=4.8 ms, Eq. 8 shows that the upper bounds for $T_{2D}$ for brine, oil, and gas are $T_{2D,b}$=29.2 ms, $T_{2D,o}$=1,406 ms, and $T_{2D,g}$=2.25 ms. Hence, $T_{2D,g}$ is located to low end of a $T_2$ spectrum and $T_{2D,o}$ is located the high end of the spectrum, and there is a gap between the $T_{2D,o}$ and the $T_{2D,b}$. Because of the influence of noise, the actual upper bound for a brine phase can be ~2*$T_{2D,b}$.

In the numerical example being considered here, the oil and the brine are well separated because $T_{2,o}=[(1/T_{2D,o})+(1/T_{2B,o})]=140$ ms>>60 ms=~2*$T_{2D,b}$. Oil-filled porosity is obtained by integrating the area under the peak.

In summary, the EDM uses differences in diffusion coefficients among the phases for setting up $T_2$ upper bounds for the phases. As long as the $T_2$ of an oil is larger than ~2*$T_{2D,b}$, the oil-filled porosity can be obtained from its separated peak.

Figure 4A:
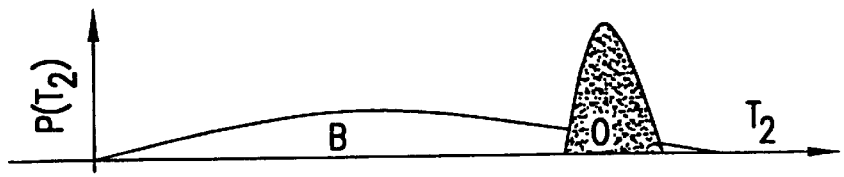
FIG. 4 illustrates the principles used for fluid typing in the Enhanced Diffusion Method (EDM) of the present invention.
Figure 4B:
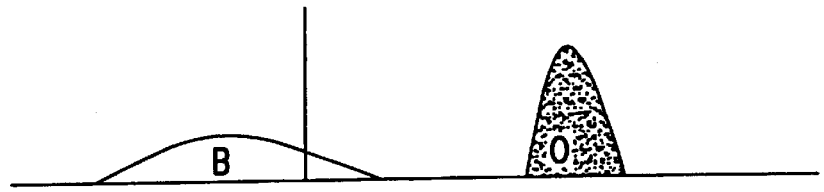

FIG. 4 illustrates the principle of the EDM. FIG. 4(a) depicts a $T_2$ spectrum without diffusion influence (G*TE~0). FIG. 4(b) shows the $T_2$ spectrum with diffusion influence (G*TE>>0). The vertical line in FIG. 4(b) is the $T_{2D,b}$, to the right of which is a separated oil peak.

EDM Data Acquisition and Processing

If only a qualitative analysis is needed, EDM data are acquired in accordance with the present invention with $T_W$~3*$T_{1,Max}$, where $T_{1,Max}$ is the maximum value of a $T_1$ spectrum for all phases, and with a large TE for separating oil from the other phases. However, for a quantitative analysis and a fast logging speed, in accordance with the present invention EDM are acquired with two $T_W$s (typically, 5000 ms and 500 ms) and a long TE (usually 4.8 ms) in two CPMG pulse sequences. In accordance with a preferred embodiment of the present invention a dual wait-time pulse sequence is run to collect the required NMR measurement data. Dual wait-time sequencing capability not requiring separate logging passes is provided by the MRIL® tool as described, for example, in co-pending application Ser. No. 08/822,567 assigned to the assignee of the present application, which is incorporated herein for all purposes. In alternative embodiments of the present invention, a single wait-time pulse sequence can also be used, since there will be $T_2$ separation between the two phases regardless of any $T_1$ contrast. Because the method to acquire data is the same as the one used in the DSM, the data processes are nearly identical except that a correction for the short component of $T_1$ of oil must be considered. More detail concerning the EDM method is found in the co-pending patent application Ser. No. 09/270,616, filed Mar. 17, 1999, the content of which is incorporated herein by reference.

Because the oil targeted for detection by this method usually has a $T_1$ distribution that includes a long component and a short component, two $T_1$ corrections must be made in accordance with the present invention for whether the processing is performed in $T_2$ domain or in time domain. In a specific embodiment, the first correction is applied to the long $T_1$ component of the oil, which has a large D. The second correction is applied to the short component (which has a small D) so that it mixes with the water signal. In the second correction, the $T_1$ distribution of the oil is needed to determine the contributions of the short components. Details of the $T_1$ corrections can be found, for example in the above application.

Applications

Figure 5:
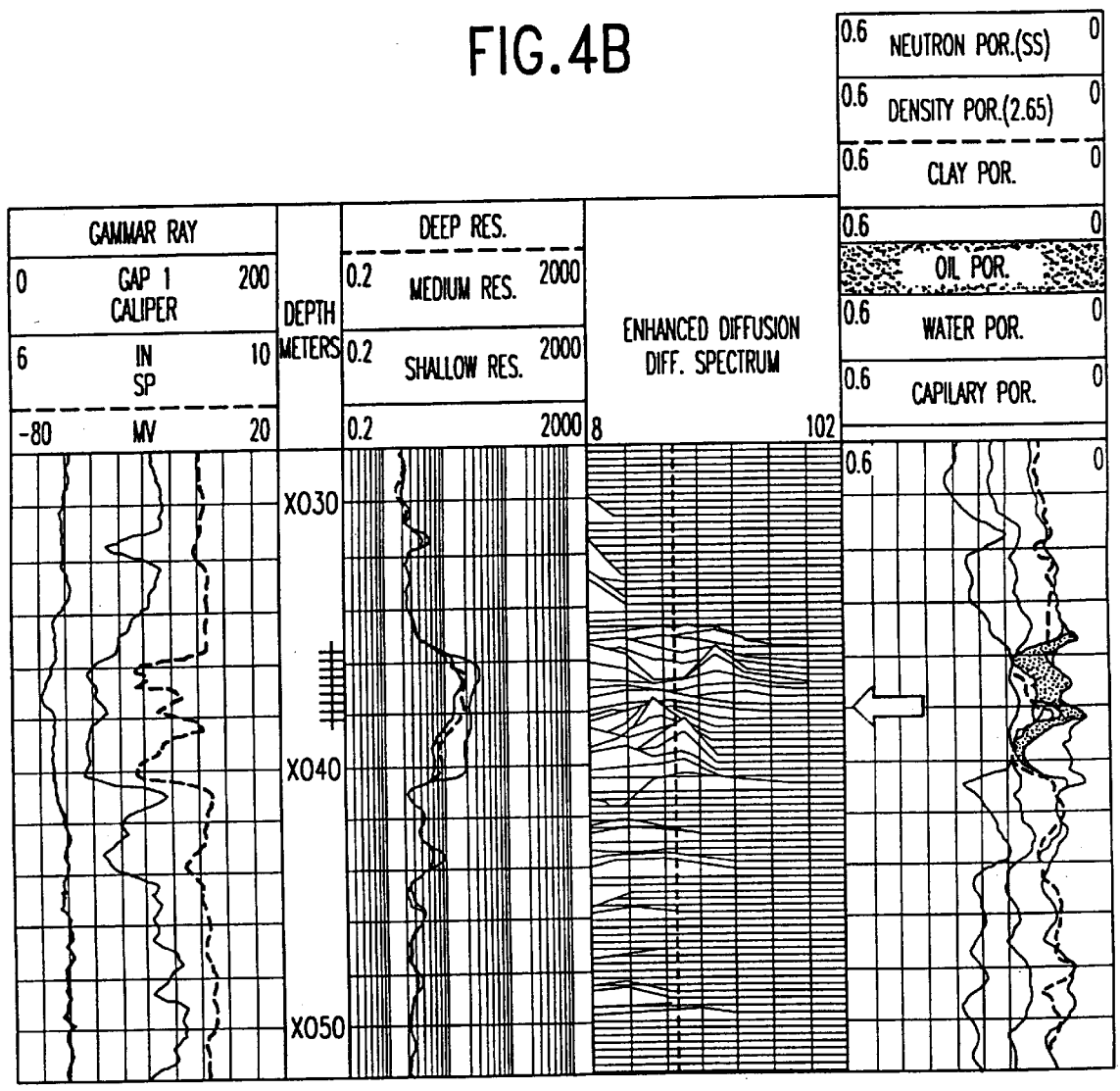
FIG. 5 shows an EDM application using $T_2$ domain analysis.

An EDM application in which $T_2$ domain analysis was used in accordance with the present invention is shown in FIG. 5. In this figure, the gamma ray, resistivity, and porosity logs shown in Tracks 1, 2, and 4 suggest a possible hydrocarbon zone at around X036. Track 3 contains the differential spectrum from the EDM logs acquired with TE=3.6 ms and $T_W$=300 ms and 3,000 ms. The dashed vertical line in Track 3 represents $T_{2D,b}$=44 ms. The oil signal is clearly seen to the right of this line. From the differential spectrum, a water/oil contact is identified at around X036, and 10% oil is produced in the surrounding interval.

Figure 6:
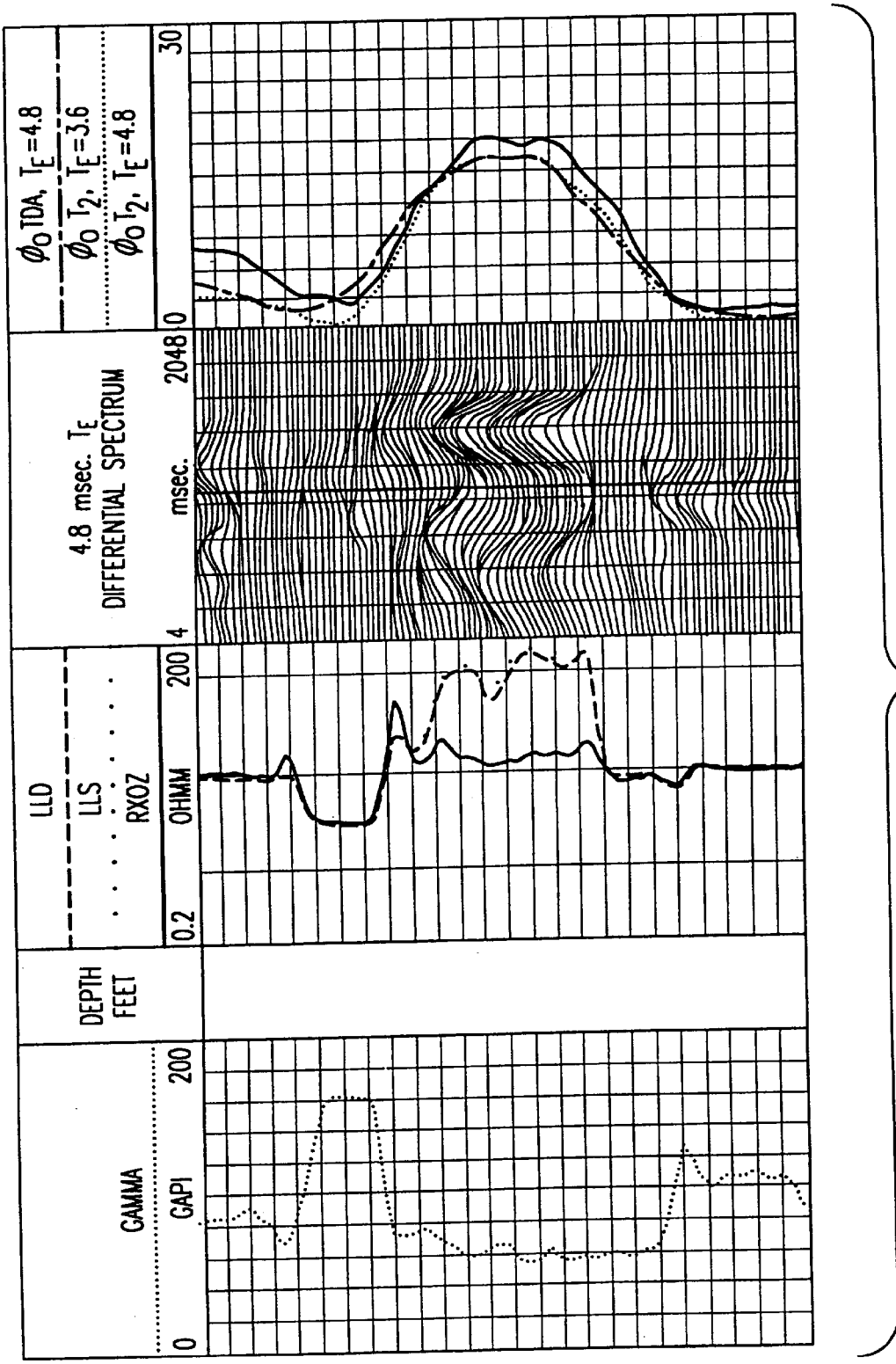
FIG. 6 is a comparison between the $T_2$ domain and TDA approaches for determining residual oil saturation (ROS) in accordance with the present invention.

FIG. 6 is a comparison between the $T_2$ domain and TDA approaches for determining residual oil saturation (ROS) in accordance with the present invention. Tracks 1 and 2 contain the gamma ray and resistivity logs, while Track 3 displays the differential spectrum for $T_W$=5,000 and 500 ms and TE=4.8 ms. Three apparent oil volumes are plotted in Track 4. The solid and dotted curves represent the oil volumes obtained from $T_2$ domain analysis using data acquired with $T_W$=5,00 ms and 5000 ms for TE=4.8 ms and 3.6 ms, respectively. The dashed curve was obtained from TDA on the data sets of TE=4.8 ms. In this example, these curves demonstrate that the two processing methods yield almost the same oil volume.

It should be noted that from a quantitative point of view, the oil porosity from a $T_2$ domain analysis may not be very accurate because the value of $T_{2D,b}$ can be influenced by an internal gradient. Accuracy can also be adversely affected by noise. Portion of brine's $T_2$ can be larger than $T_{2D,b}$. These considerations should be taken into account in practical applications.

Figure 7:
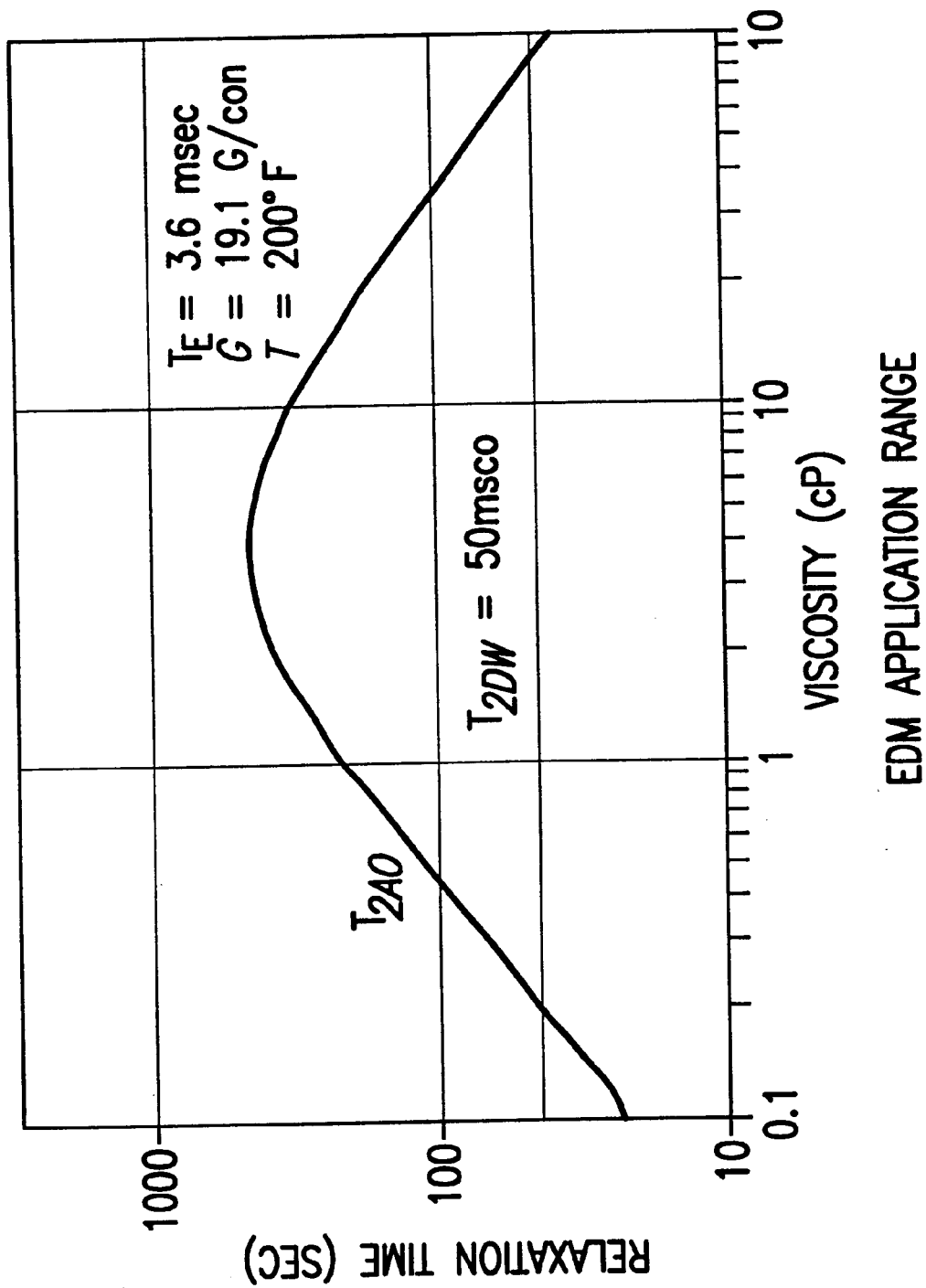
FIG. 7 shows a typical application range of EDM in accordance with the present invention.

As noted above, the DSM provides typing of gas and light oil. The EDM expands the fluid-typing range to medium oil. FIG. 7 shows a typical application range of EDM. To plot this figure, Eq. 6, 8, and 14 are used with TE=3.6 ms, G=19.1 gauss/cm, T=200° F. If the oil-water $T_2$ contrast is chosen as 2, then the EDM can be applied to type oil with viscosity from approximately 0.4 to 40 cp, with the maximum contrast occurring between 4 and 10 cp.

In accordance with the present invention, the EDM can be applied in carbonate reservoirs. Note that DSM typing may not give good results in such reservoirs because of long $T_2$ and $T_1$ components for the brine phase. This is an example of how the flexibility provided by the present invention enables accurate analysis of the formation fluids dependent on the particular conditions.

3. The Shift Spectrum Method

In accordance with the present invention, the SSM is used for gas and oil typing. In principle, the SSM is also a diffusion contrast method and thus is suited for use with the gradient NMR tools. In a preferred embodiment, it applies two different TEs and a long $T_W \geq (2 \text{ to } 3)*T_{1,Max}$ in two CPMG pulse sequences. Relating to the $T_2$ spectrum that results from the short TE, the $T_2$ spectrum from the long TE due to diffusion effect is shifted to the low end of the $T_2$, and the spectrum is also compressed. If the gas signal is shifted to the dead time of an MRIL tool when collecting long TE data, then the gas signal cannot be detected in the long TE data; however, the gas signal is present in the short TE data. By taking the difference between the long and short TE data and ignoring the diffusion influence of brine and oil, only gas signal is obtained.

The net magnetization for the difference of the two CPMG trains is $$\Delta M(t) = \Sigma M_{0,i=o,b,g} * \{\exp\{-t*[1/T_{2B,i}+D_i*(\gamma*TE_1*G)^2/12+1/T_{2S,i}]\} - \exp\{-t*[1/T_{2B,i}+D_i*(\gamma*TE_2*G)^2/12+1/T_{2S,i}]\}\} \quad (20)$$

If $TE_1=1.2$ ms and $TE_2=2.4$ ms, and the values of the parameters in Table 2 are used, then $$\Delta M(t)_g = M_{0,g} * \exp\{-t*[D_i*(\gamma*TE_1*G)^2/12]\} \quad (21)$$

$$\Delta M(t)_o = M_{0,o} * \exp(-t*1/T_{2B,o}) * \{\exp\{-t*[D_o*(\gamma*TE_1*G)^2/12]\} - \exp\{-t*[D_o*(\gamma*TE_2*G)^2/12]\}\} \sim 0 \quad (22)$$

$$M(t)_b = M_{0,b} * \exp(-t*1/T_{2S,b}) * \{\exp\{-t[*D_b*(\gamma*TE_1*G)^2/12]\} - \exp\{-t*[D_b*(\gamma*TE_2*G)^2/12]\}\} \sim 0 \quad (23)$$

Hence, for these two TE values, when oil and brine diffusion influences on $T_2$ can be ignored, only gas signal is left in $\Delta M(t)$.

Figure 8:
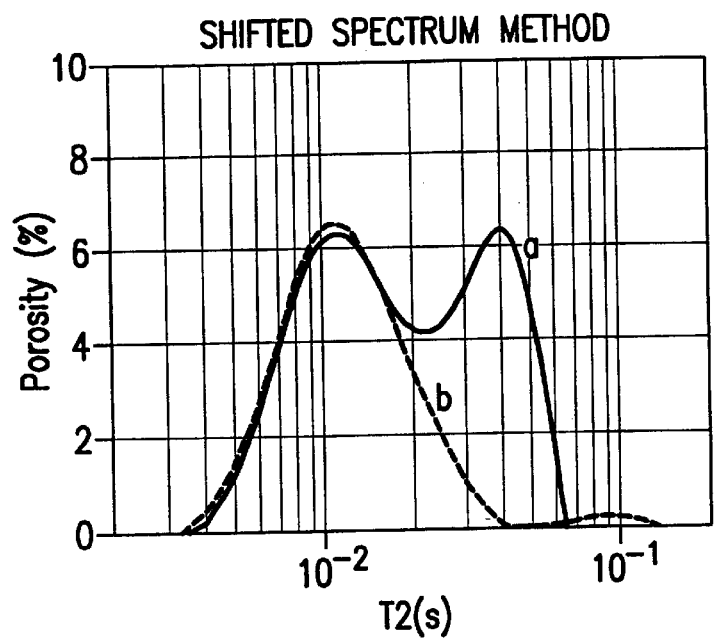
FIG. 8 illustrates the principles used for fluid typing in the Shift Spectrum Method (SSM) used in accordance with the present invention.

FIG. 8 illustrates the principle of SSM used as a fluid typing method in accordance with the present invention. The solid curve, shown as 'a' in the figure, represents the spectrum obtained when TE=1.2 ms, and the dashed curve, shown as 'b', represents the spectrum obtained when TE=4.8 ms. The 40 ms peak in the solid curve is gas and is shifted out in the 4.8 ms spectrum. The gas signal is found by subtracting the dashed curve from the solid curve.

Data Acquisition and Processing

Data for use in the SSM are usually acquired with TE set at 1.2 and 3.6 ms and $T_W=8$s. This method has a much longer pulse cycle time, which is the time for acquiring two CPMG data sets. The cycle time is approximately 16 seconds for SSM, but only 5.5 seconds for EDM. SSM data can be processed in accordance with this invention by either $T_2$ domain analysis or TDA. In a preferred embodiment, the processing is the same as for the DSM, except that the matched filter in TDA for gas is different because the diffusion influence on SSM must be considered.

Applications

In accordance with the present invention, the SSM can be applied to determine gas signals. See, e.g. Mardon, D., et al.: "Characterization of Light Hydrocarbon-Bearing Reservoirs by Gradient NMR Well Logging: A Gulf of Mexico Case Study," paper SPE 36520 presented at the 1996 SPE Annual Technical Conference and Exhibition, Denver, Colo., U.S.A., Oct. 6–9, 1996. In the above reference, TE=1.2 and 2.4 ms is used in CPMG pulse sequences to obtain two $T_2$ spectra. Comparing the spectra and using gamma ray, resistivity, and neutron-density logs, it was found that the water and light-oil signals remain, but the gas signal is shifted to below detectable levels for the 2.4 ms data.

SSM dual-TE logging is more useful in a more viscous oil ($\eta \sim 20$ cp). Such oil has a much smaller diffusion coefficient than water. By using the diffusion contrast between water and the more viscous oil, an empirical crossplot of $T_2$, and D can be created, where $T_{2I}=[1/T_{2B}+1/T_{2S}]^{-1}$. See Coates, G. R., et al.: "Applying Log Measurements of Restricted Diffusion and $T_2$ to Formation Evaluation," paper P presented at the $36^{th}$ Annual SPWLA Logging Symposium, Paris, France, Jun. 26–29, 1995. The following two equations were used to calculate $T_2$, and D from the data sets acquired with two TE values.

$$(1/T_2)_{TE1} = 1/T_{2I} + D*(\gamma*TE_1*G)^2/12 \quad (24)$$

$$(1/T_2)_{TE2} = 1/T_{2I} + D*(\gamma*TE_2*G)^2/12 \quad (25)$$

Water saturation and pore size are determined from the crossplot. This crossplot is applied to determine oil-filled porosity in a well in western Canada. A similar approach can be applied, but obtained $T_{2i}$ and D from the spin-echo time domain to determine oil-filled porosity.

4. The Total Porosity Method (TPM

The DSM, SSM, and EDM are specially designed and used in accordance with the present invention for hydrocarbon typing. The TPM used in accordance with the present invention is good for distinguishing brine-related porosity components: clay-bound water, capillary-bound water, and movable water. See Prammer, M. G., et al.: "Measurements of Clay-Bound Water and Total Porosity by Magnetic Resonance Logging", paper SPE 36522 presented at the 1996 SPE Annual Technical Conference and Exhibition, Denver, Colo., U.S.A., Oct. 6–9, 1996; and Coates, G.R., et al.: "Applying NMR Total and Effective Porosity to Formation Evaluation," paper SPE 38736 presented at the 1997 SPE Annual Technical Conference and Exhibition, San Antonio, Tex., U.S.A., Oct. 5–8, 1997.

Bound water saturation is a very important parameter for estimating formation production. To accurately determine the volume of formation occupied by immovable water, in accordance with the present invention, the fast decay signal, which arises mainly from clay-bound-water, must be recorded. Recording this decay signal requires a short TE and a good SNR.

Figure 9:
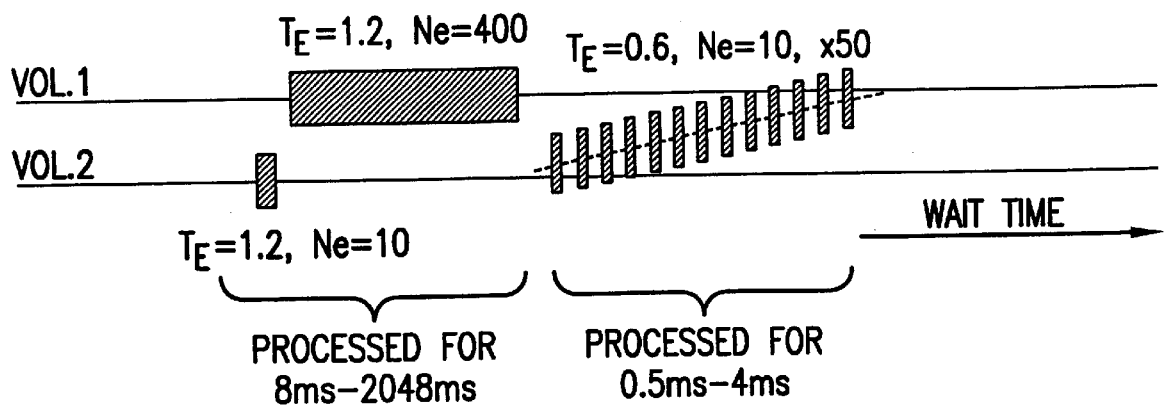
FIG. 9 illustrates pulse sequences used in accordance with the present invention for the Total Porosity Method (TPM).

In accordance with the present invention, a modified MRIL®-C tool can be used along with pulse sequences, as shown in FIG. 9 in a preferred embodiment for the TPM. These pulse sequences have two parts.

The first part is a regular pulse sequence having a long $T_W$ for full recovery of magnetization between measurements. This part usually uses a 1.2 ms echo spacing time, and acquires 400 echoes. Effective porosity is obtained from the data.

The second part is designed to obtain the clay-bound signal ($T_2 < 2.5$ ms). This part has a short $T_W$ (20 ms), a short TE (0.6 ms), a short echo train (8 to 10 echoes), and 50 pulse repetitions. The short $T_W$ can not provide a $T_2$ spectrum with full recovery, but it is long enough for full recovery of the clay-bound $T_2$. The TE=0.6 ms is primarily used to resolve $T_2$ values less than or equal to 1 ms. The repetitions is used to increase S/N of the clay-bound signal.

Figure 10:
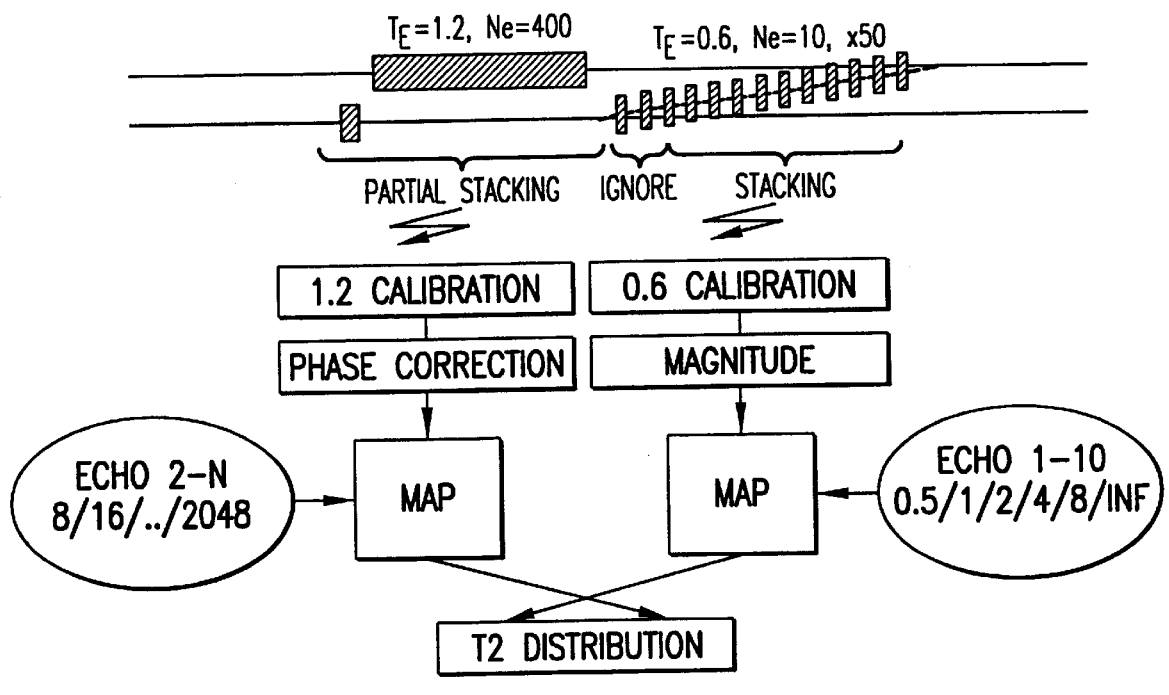
FIG. 10 illustrates a data processing mechanism used in accordance with the present invention as part of the TPM.

The data acquisition process provides two data sets with different S/N. To obtain the total porosity, these two data sets must be combined. In a preferred embodiment, a $T_2$ inversion algorithm for the data sets by using two inversions and a cutoff method is used. FIG. 10 indicates how the data are processed. The data sets with high and low S/N are inverted separately by fixing different $T_2$ values. Data combination is accomplished simply by using the first four $T_2$ components (0.5, 1, 2, and 4 ms) from the short echo data and all of the components from 8 ms and up obtaining from the inversion of the long echo data. This method results in a $T_2$ distribution that is discontinuous around the cutoff values, which are 4 and 8 ms.

Recently, an algorithm has been developed for simultaneous inversion of the data sets with different SNR. The resulting $T_2$ spectrum for total porosity is continuous, and has more information on clay-bound water.

In the $T_2$ distribution, the porosity occupied by clay-bound-water is proportional to the area where $T_2<2.5$ ms. In a sandstone reservoir, the porosity occupied by capillary-bound-water is proportional to the area in which 2.5 ms$<T_2<35$ ms; in a carbonate reservoir, these bounds are given by 2.5 ms$<T_2<100$ ms. The remainder of the area under the spectrum (i.e., $T_2>35$ ms for the sandstone and $T_2>100$ ms for the carbonate) is proportional to the porosity occupied by movable fluids.

Figure 11:
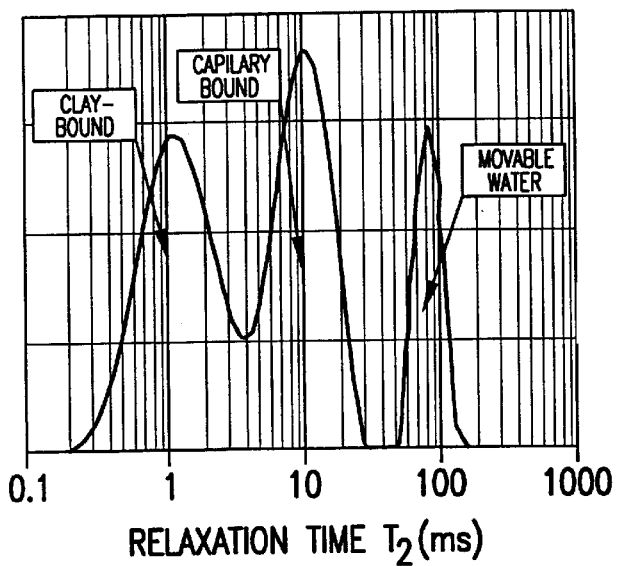
FIG. 11 illustrates a $T_2$ spectrum obtained through TPM.

FIG. 11 is a $T_2$ spectrum obtained through TPM. This spectrum is divided into the regions that correspond to clay-bound, capillary-bound, and movable water.

If only information about bound-water is needed, a short $T_W$ and smaller echo number can be used because $T_1$ and $T_2$ of bound-water are short. This application has been demonstrated with a CMR tool, using TE=0.2 ms, $T_W$=0.25 s, and 165 echoes in a sandstone reservoir, and TE=0.2 ms, $T_W$=0.75 s, and 500 echoes in a carbonate reservoir. Logging with these parameters can be fast (3,600 ft/hr in sandstones and 1,200 ft/hr in carbonates).

5. The Injecting Contrast Agent Method (ICΔM)

The ICAM is a method for accurately determining residual oil saturation (ROS) in open hole, although the need to inject a contrast agent can sometimes be an inconvenience. The most common agents used in the ICAM are Mn-EDTA and $MnCl_2$. Through the invasion of dosed mud or through direct injection of the contrast agent, the agent mixes with formation brine. Because of the short $T_2$ of the resulting mixture, the signal from the brine cannot be detected. However, the oil signal is not influenced by the agent and can be measured by an NMRL tool. Further details concerning this method can be found, for example in U.S. Pat. No. 3,657,730, which is incorporated herein for all purposes.

Recently, a cheaper contrast agent ($MnCl_2$) and a faster NMR doping and logging procedure have been discovered. See Horkowitz, J. P., et al.: "Residual Oil Saturation Measurements in Carbonates With Pulsed NMR Logs," *The Log Analyst* (March–April 1997). In accordance with a preferred embodiment, this agent and procedure can be used to determine ROS in a carbonate reservoir in west Texas. $Mn^{++}$ iron in the new contrast agent has greater relaxivity for water protons than Mn-EDTA, so less dope is required. The reduction in time is possible because there is no need to pack off and inject in the target zoom.

For determining ROS, the method of the present invention only reduces the $T_2$ of the $MnCl_2$-$H_2O$ mixture to separate the oil signal. From the oil and the mixture peaks, ROS and porosity can be obtained.

Figure 12:
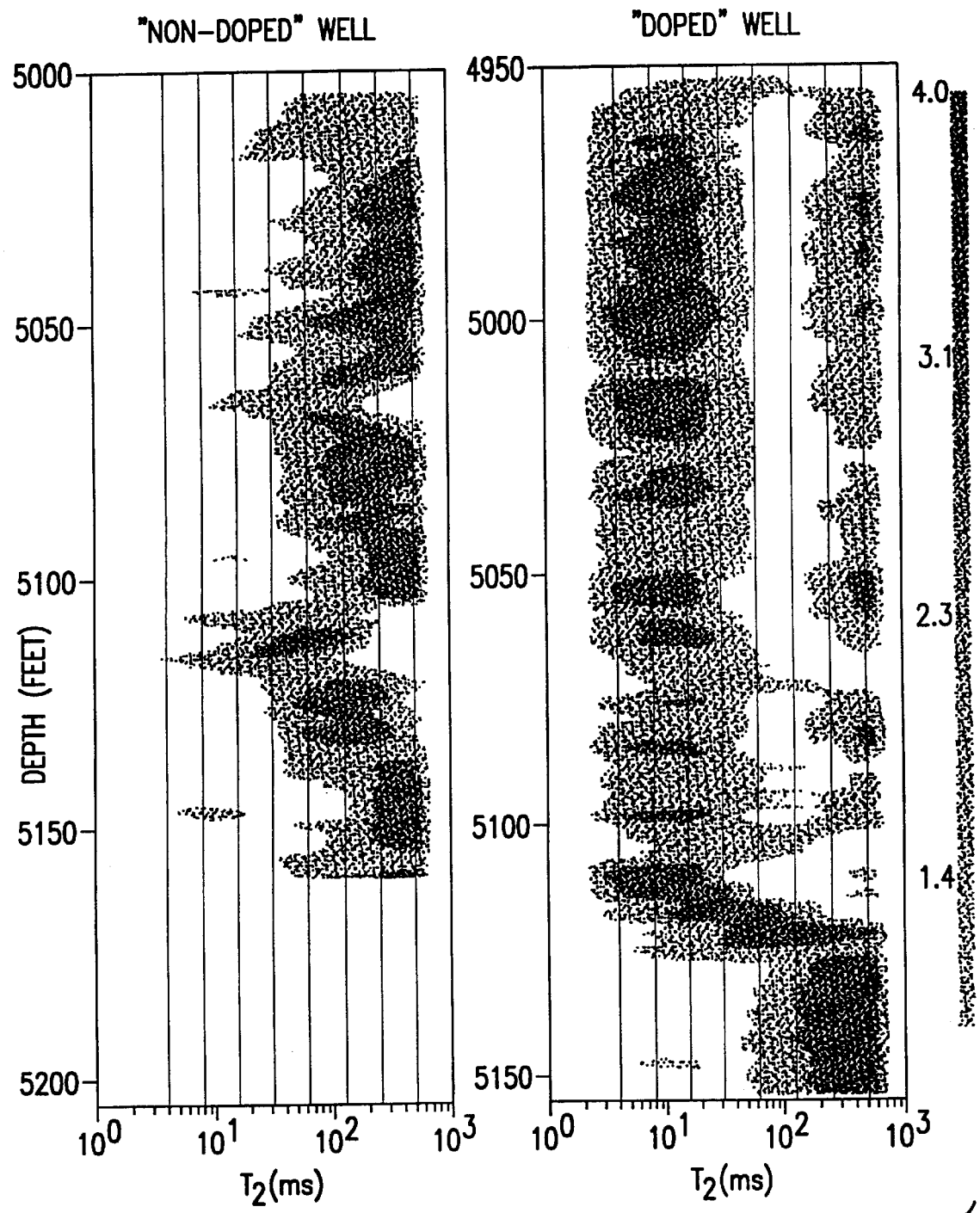
FIG. 12 is an example of using $MnCl_2$ in an Injecting Contrast Agent Method (ICAM) used in accordance with the present invention for obtaining Residual Oil Saturation (ROS) and porosity.

FIG. 12 is an example of using $MnCl_2$ in ICAM for obtaining ROS and porosity. Track 1 is a $T_2$ distribution (spectrum) for a "non-doped" well, and the Track 2 is a $T_2$ distribution (spectrum) for the "doped" well. Comparison of the two spectra reveals that the water signal is shifted to 10 ms to 20 ms, while the oil signal is still at 500 ms after the doping with $MnCl_2$. A $T_2$ cutoff value for the oil signal is found from the $T_2$ distribution as 90 ms. The oil-filled porosity can be obtained from the total area of $T_2>90$ ms. Because $MnCl_2$ shifts only the water signal, the total signal from the oil and the water provides porosity. Therefore, the ROS is the ratio of the oil-filled porosity to the porosity.

Miscellaneous

Five NMR-based methods for fluid typing have been reviewed from the standpoint of principles, data acquisition and processing, and applications, as used in preferred embodiments of the present invention. By using a suitable combination of these methods, the individual porosities occupied by clay-bound water, capillary-bound water, movable water, gas, light oil, medium oil, and residual oil can be determined with high accuracy under different formation conditions.

It should be apparent that knowledge of formation conditions, such as formation temperature, formation pressure, and fluid viscosity are crucial in obtaining high-quality logging data, and in selecting the optimum methods to be used in fluid typing. In particular, while the discussion above focuses solely on NMR-based methods, various other logging methods to enhance the accuracy of the measurement and data interpretation processes practiced in accordance with the present invention. For example, conventional neutron, density, sonic and resistivity logs can be used in addition to or in combination with the methods described above for improved results.

Although the present invention has been described in connection with the preferred embodiments, it is not intended to be limited to these embodiments but rather is intended to cover such modifications, alternatives, and equivalents as can be reasonably included within the spirit and scope of the invention as defined by the following claims.

What is claimed is:

1. A method for fluid typing of a geological environment using nuclear magnetic resonance (NMR) measurements comprising:

determining a set of parameters for a gradient NMR measurement, obtaining a pulsed NMR log using the determined set of parameters; and selecting from the NMR log an optimum contrast mechanism and corresponding measurement parameters for fluid typing of the geological environments, wherein the set of determined parameters comprises the interecho spacing $T_E$ of a pulsed NMR sequence, and the interecho spacing $T_E$ is determined at least on the basis of the expected viscosity of the oil in the formation.

2. The method of claim 1, wherein the set of determined parameters comprises the magnetic field gradient G of the NMR measurement.

3. The method of claim 1, wherein the set of determined parameters comprises the wait time $T_W$ of the NMR measurement.

4. The method of claim 1, wherein said optimum contrast mechanism is based on diffusion.

5. The method of claim 1, wherein said optimum contrast mechanism is based on relaxation.

6. The method of claim 1, wherein said optimum contrast mechanism is based on hydrogen index contrast.

7. The method of claim 1, wherein the step of selecting measurement parameters for fluid typing comprises selecting parameters that correspond to one or more of the DSM, EDM, SSM, TPM, and ICAM fluid typing methods.

8. A method for fluid typing of a geological environment using nuclear magnetic resonance (NMR) measurements comprising:

conducting a first NMR measurement using a first predetermined set of measurement parameters;

comparing said first NMR measurement results to a predetermined set of criteria to estimate which types of fluids may have produced the first NMR measurement results;

selecting an appropriate type of contrast mechanism and a corresponding second set measurement parameters for the estimated types of fluids; and conducting a second NMR measurement using said second set of parameters to increase the accuracy of the fluid typing determination in case said second set of parameters is different from said first set of parameters.

9. The method of claim 8 wherein the first and the second set of parameters correspond to one or more of the DSM, EDM, SSM, TPM, and ICAM fluid typing methods.

10. The method of claim 8, wherein at least one of the first and second set of measurement parameters comprises the interecho spacing $T_E$ of a pulsed NMR sequence.

11. The method of claim 10, wherein the interecho spacing $T_E$ is determined at least on the basis of the expected viscosity of the oil in the formation.

12. The method of claim 8, wherein at least one of the first and second set of measurement parameters comprises the wait time $T_W$ of the NMR measurement.

13. The method of claim 8, wherein at least one of the first and second set of measurement parameters comprises the magnetic field gradient of the NMR measurement.

14. The method of claim 8, wherein the selected contrast mechanism is based on one of diffusion, relaxation and hydrogen index contrast.

15. The method of claim 8, wherein the predetermined set of criteria in the step of comparing is based on one of: theoretical models or external measurements.

16. A computer storage medium storing a software program to be executed on a computer, comprising:

a first software application for capturing NMR data concerning a first measurement;

a second software application, for comparing the first measurement data to pre-set rules determining the optimum contrast mechanism for use in the environment; and a third software application, for providing a predetermined set of measurement parameters according to the determined optimum contrast mechanism.

17. The computer storage medium of claim 16, wherein the predetermined set of measurement parameters in the third software application correspond to one or more of the DSM, EDM, SSM, TPM, and ICAM fluid typing methods.

18. The computer storage medium of claim 16, wherein the predetermined set of measurement parameters comprises the interecho spacing $T_E$ of a pulsed NMR sequence.

19. The computer storage medium of claim 18, wherein the interecho spacing $T_E$ is determined at least on the basis of the expected viscosity of the oil in the formation.

20. The computer storage medium of claim 16, wherein the predetermined set of measurement parameters comprises the magnetic field gradient G of the NMR measurement.

21. The computer storage medium of claim 16, wherein the predetermined set of measurement parameters comprises the wait time $T_W$ of the NMR measurement.

22. The computer storage medium of claim 16, wherein said optimum contrast mechanism is based on one of diffusion, relaxation and hydrogen index contrast.

23. The computer storage medium of claim 16, wherein at least one of the first, second and third software application program is stored on a CD ROM.

24. An apparatus for fluid typing of a geological environment using nuclear magnetic resonance (NMR) measurements comprising:

a logging tool capable of conducting NMR measurements in a borehole;

data storage for storing NMR log data corresponding to one or more NMR measurements each measurement using a predetermined set of measurement parameters;

a computer processor configured to execute a software application program for selecting from NMR log data an optimum contrast mechanism and corresponding measurement parameters for fluid typing of the geological environment; and a measurement cycle controller providing control signals to the logging tool for conducting NMR measurements based on input from said processor, wherein the set of determined parameters comprises the interecho spacing TE of a pulsed NMR sequence and the interecho spacing $T_E$ is determined at least on the basis of the expected viscosity of the oil in the formation.

25. The apparatus of claim 24, wherein the set of determined parameters comprises the magnetic field gradient G of the NMR measurement.

26. The apparatus of claim 24, wherein the set of determined parameters comprises the wait time $T_W$ of the NMR measurement.

27. The apparatus of claim 24, further comprising a display for indicating the selection of measurement parameters to a human operator.

28. The apparatus of claim 12, wherein the software application program is stored on a CD ROM.

29. The apparatus of claim 24, wherein the logging tool is capable of conducting multi-contrast NMR measurements.

30. An apparatus for fluid typing of a geological environment using nuclear magnetic resonance (NMR) measurements comprising:

a logging tool capable of conducting NMR measurements in a borehole;

data storage for storing NMR log data corresponding to one or more NMR measurements each measurement using a predetermined set of measurement parameters;

a computer processor configured to execute a software application program for selecting from NMR log data an optimum contrast mechanism and corresponding measurement parameters for fluid typing of the geological environment; and a measurement cycle controller providing control signals to the logging tool for conducting NMR measurements based on input from said processor, wherein the logging tool has a dual wait-time sequencing capability.

31. The apparatus of claim 30, wherein the logging tool is capable of conducting multi-contrast NMR measurements.

32. The apparatus of claim 30, wherein the computer processor is configured to compare NMR measurement data to a predetermined set of criteria to estimate which types of fluids may have produced the NMR measurement results.

33. The apparatus of claim 30, wherein measurement parameters for fluid typing correspond to one or more of the DSM, EDM, SSM, TPM, and ICAM fluid typing methods.

34. The apparatus of claim 30, wherein the computer processor is configured to execute a software application program combining NMR log data with data from one or more of neutron, density, sonic and resistivity logs.

* * * * *